(12) United States Patent
Murphy et al.

(10) Patent No.: US 8,794,676 B2
(45) Date of Patent: Aug. 5, 2014

(54) DEVICE AND METHOD FOR CONNECTING FLUID CONDUITS

(75) Inventors: James P. Murphy, Franklin, MA (US); Joseph Michienzi, Plainville, MA (US); David Prentice, Millville, MA (US); Sylvain Cormier, Mendon, MA (US)

(73) Assignee: Waters Technologies Corporation, Milford, MA (US)

( * ) Notice: Subject to any disclaimer, the term of this patent is extended or adjusted under 35 U.S.C. 154(b) by 482 days.

(21) Appl. No.: 12/993,294

(22) PCT Filed: May 21, 2009

(86) PCT No.: PCT/US2009/044880
§ 371 (c)(1),
(2), (4) Date: Jan. 13, 2011

(87) PCT Pub. No.: WO2009/146290
PCT Pub. Date: Dec. 3, 2009

(65) Prior Publication Data
US 2011/0198842 A1    Aug. 18, 2011

Related U.S. Application Data

(60) Provisional application No. 61/057,214, filed on May 30, 2008.

(51) Int. Cl.
*F16L 25/00* (2006.01)
(52) U.S. Cl.
USPC .................. 285/332.1; 285/330; 285/389
(58) Field of Classification Search
USPC ............... 285/384, 385, 386–389, 330, 332, 285/332.1
See application file for complete search history.

(56) References Cited

U.S. PATENT DOCUMENTS

| 1,889,778 A | 12/1932 | Dobrick |
| 3,992,043 A | 11/1976 | Whitley |

(Continued)

FOREIGN PATENT DOCUMENTS

| EP | 0053768 | 6/1982 |
| GB | 2 431 971 B | 6/2007 |

(Continued)

OTHER PUBLICATIONS

International Search Report, Dated: Jul. 14, 2009, 1 Page.

(Continued)

*Primary Examiner* — James Hewitt
*Assistant Examiner* — Jay R Ripley
(74) *Attorney, Agent, or Firm* — Muirhead and Saturnelli, LLC

(57) ABSTRACT

A connector for connecting a first conduit to a second conduit including a body having a passageway therethrough, a first cavity and a second cavity, a first sealing member, a second sealing member, a first compression, a second compression fitting, a first set of one or more keys and one or more mated key ways for preventing rotation of the first conduit when the first sealing member is compressed, and a second set of one or more keys and one or more mated key ways for preventing rotation of the second conduit when the second sealing member is compressed, wherein each of the first cavity and the second cavity in the body is configured to receive one of the sealing members or a detachable holder configured to receive one of the sealing members.

14 Claims, 23 Drawing Sheets

(56) References Cited

U.S. PATENT DOCUMENTS

| | | | |
|---|---|---|---|
| 4,083,702 A | 4/1978 | Hartigan et al. | |
| 4,283,280 A | 8/1981 | Brownlee | |
| 4,313,828 A | 2/1982 | Brownlee | |
| 4,619,473 A | 10/1986 | Someya | |
| 4,669,756 A | 6/1987 | Cassaday et al. | |
| RE32,482 E | 8/1987 | Anderson | |
| 4,690,437 A | 9/1987 | Anderson | |
| 4,713,963 A * | 12/1987 | Sharp | 73/23.37 |
| 4,776,618 A | 10/1988 | Barree | |
| 4,787,656 A | 11/1988 | Ryder | |
| 4,989,974 A | 2/1991 | Anton et al. | |
| 5,068,494 A * | 11/1991 | Bolante | 174/654 |
| 5,080,785 A * | 1/1992 | Allington et al. | 210/198.2 |
| 5,234,235 A | 8/1993 | Worden | |
| 5,288,113 A | 2/1994 | Silvis et al. | |
| 5,364,521 A | 11/1994 | Zimmermann | |
| 5,503,187 A * | 4/1996 | Simmons et al. | 138/89 |
| 5,536,049 A * | 7/1996 | Coules et al. | 285/137.11 |
| 5,540,464 A | 7/1996 | Picha | |
| 5,578,157 A | 11/1996 | Higdon | |
| 5,582,723 A | 12/1996 | Boone et al. | |
| 5,601,785 A | 2/1997 | Higdon | |
| 6,102,449 A | 8/2000 | Welsh | |
| 6,190,616 B1 | 2/2001 | Jovanovich et al. | |
| 6,494,500 B1 | 12/2002 | Todosiev et al. | |
| 6,667,474 B1 | 12/2003 | Abramson et al. | |
| 7,265,349 B2 | 9/2007 | Park | |
| 2001/0007641 A1 * | 7/2001 | Jovanovich et al. | 422/99 |
| 2002/0117854 A1 * | 8/2002 | Thermos et al. | 285/330 |
| 2002/0195150 A1 | 12/2002 | Schick | |
| 2005/0072916 A1 | 4/2005 | Park | |
| 2005/0077222 A1 | 4/2005 | Dawes | |
| 2005/0199540 A1 | 9/2005 | Zelechonok et al. | |
| 2005/0230498 A1 | 10/2005 | Ruediger et al. | |
| 2006/0113794 A1 * | 6/2006 | Plant et al. | 285/339 |
| 2007/0164562 A1 | 7/2007 | Valaskovic et al. | |
| 2008/0007048 A1 * | 1/2008 | Benoit et al. | 285/247 |
| 2008/0038152 A1 * | 2/2008 | Van Pelt | 422/63 |

FOREIGN PATENT DOCUMENTS

| | | |
|---|---|---|
| JP | 04-194749 | 7/1992 |
| JP | 11-174037 | 7/1999 |
| JP | 2006-153603 | 6/2006 |
| WO | WO 01/73338 A1 | 10/2001 |
| WO | WO 2006/083597 A2 | 8/2006 |
| WO | WO 2006/091952 A1 | 8/2006 |

OTHER PUBLICATIONS

Japanese Application No. 3241653 A Published Abstract, 1991.

* cited by examiner

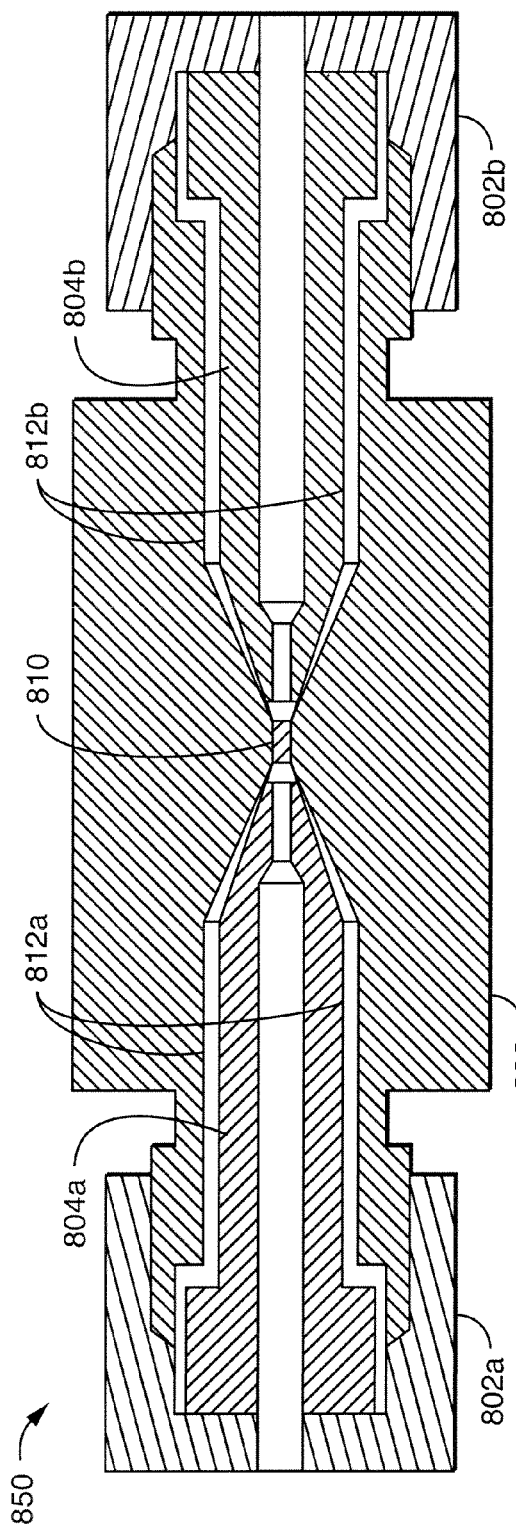
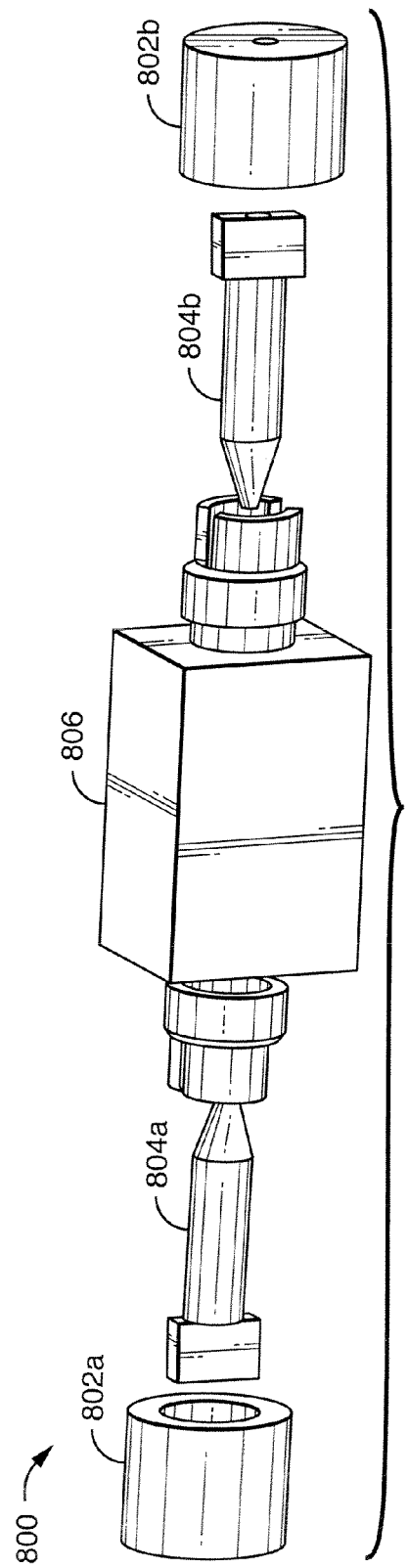
FIG. 4A
FIG. 4B

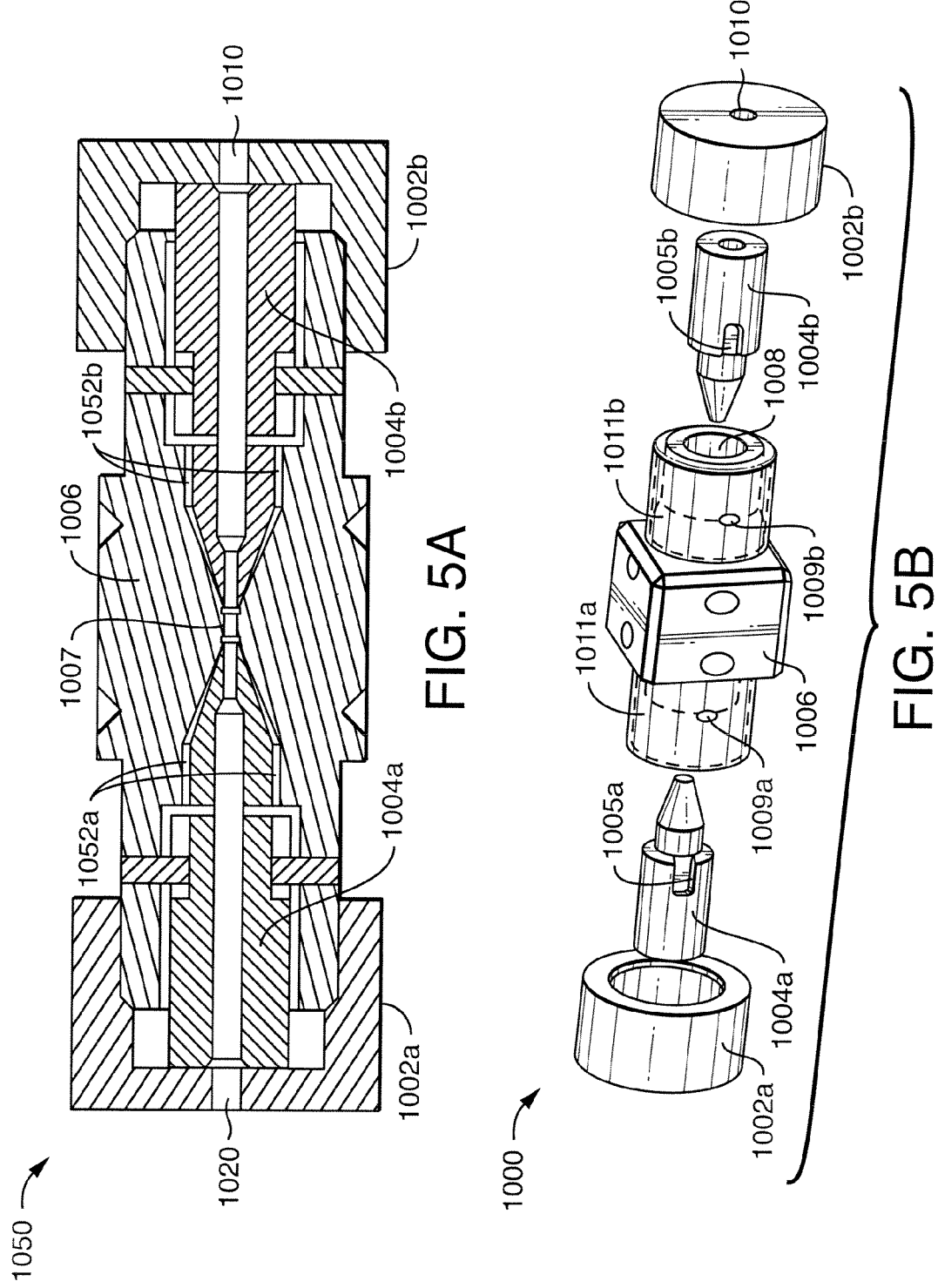

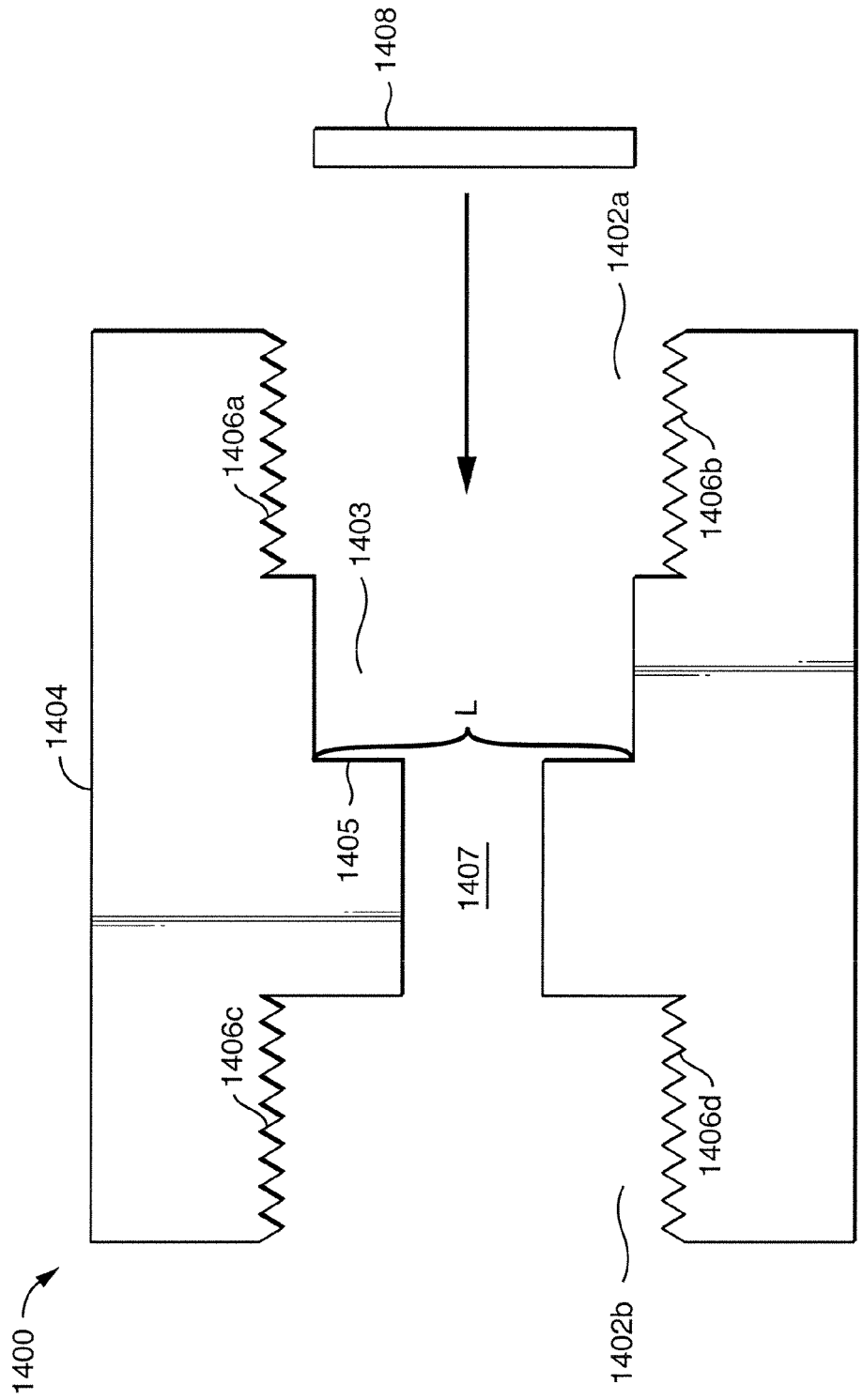

1430

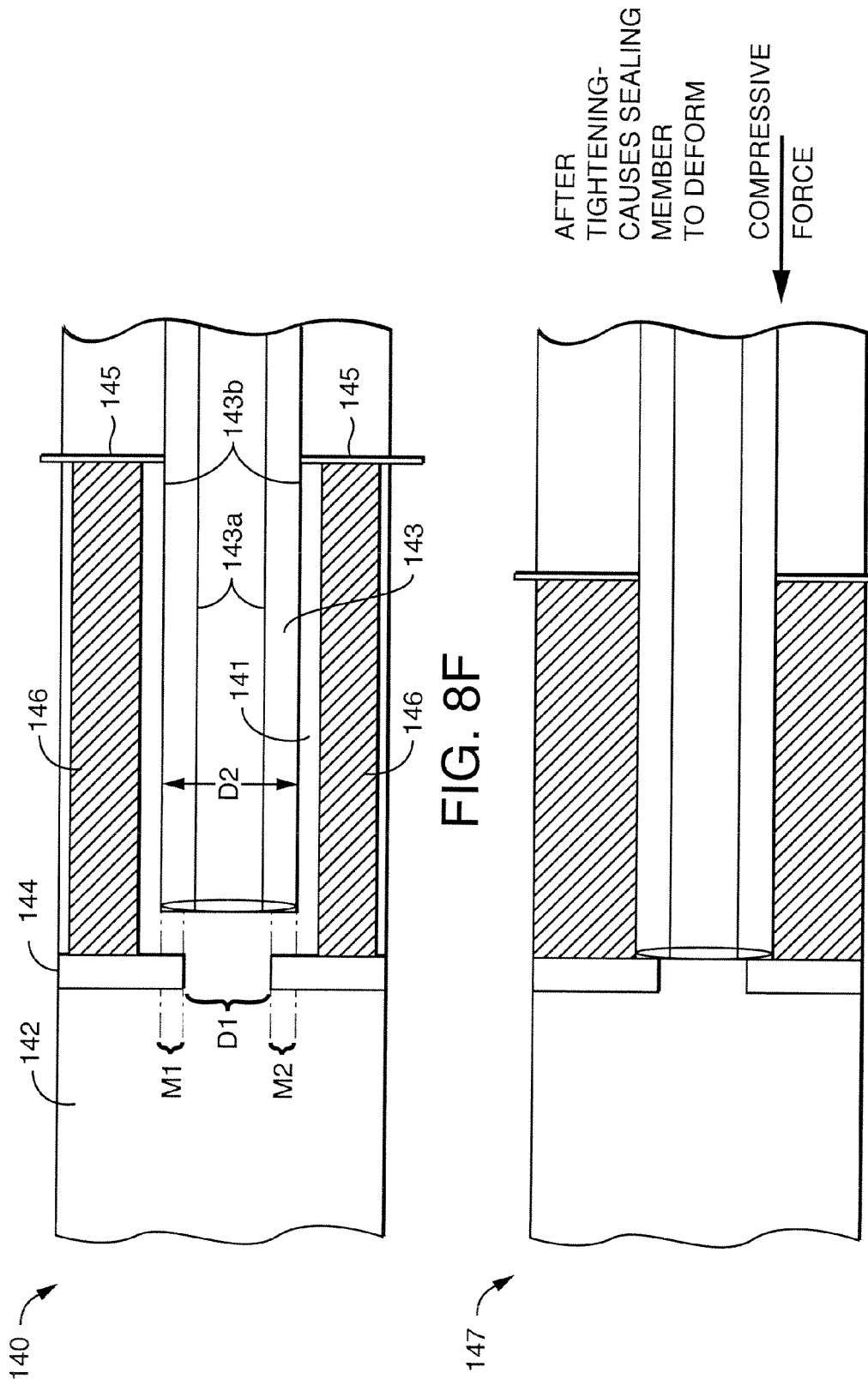

DEVICE AND METHOD FOR CONNECTING FLUID CONDUITS

CROSS-REFERENCE TO RELATED APPLICATIONS

This application is the National Stage of International Application No. PCT/US2009/044880, filed May 21, 2009, which claims priority to U.S. Provisional Application No. 61/057,214, filed May 30, 2008, all of which are hereby incorporated by reference.

TECHNICAL FIELD

The invention generally relates to connectors, and more particularly to connecting fluid-bearing conduits.

BACKGROUND INFORMATION

Instruments may utilize conduits for transportation of process fluids and sample compounds and/or for separation of sample compounds. For example, an instrument that performs liquid chromatograph (LC) may include conduits. In connection with performing analysis on fluids, it may be necessary to provide a fluidic connection between two conduits to facilitate a flow path for the fluid from a first conduit to a second conduit. Such connections should generally be leak resistant. Such a connection may be provided, for example, when interfacing different instruments or to more generally provide a fluidic connection between conduits at two points in a fluid path. The conduit may be made of a material, such as fused silica, a metal such as steel, and the like. The two conduits being connected may be made of the same or different materials. Existing devices and techniques for providing such a fluidic connection between two conduits may apply axial, radial, and/or rotational forces to the two conduits using a variety of different arrangements. One approach is to use a compression screw and ferrule. In one arrangement for connecting two conduits, each conduit is inserted in a through hole of a ferrule. The ferrules are then inserted into cavities at opposite ends of a through hole of a connector body. Openings of the cavities of the connector body may be threaded for use with a mated threaded compression screw. As a compression screw is tightened, forces are exerted on the ferrule causing the ferrule to tighten around the conduit inserted therethrough. Tightening of the compression screw causes the ferrule to press against walls within the interior of the connector body to provide a fluidic seal. As the compression screw is tightened, forces are exerted on the two conduits within the ferrules causing the two ferrules, and thus the two conduits therein, to rotate and also move in a horizontal direction towards one another so that surfaces of the exposed ends of the conduits come into contact with one another. In connection with the foregoing, a problem may occur when one or more of the two conduits are made of a material such as fused silica. When the surfaces of the two conduits come together due to the forces applied, fracturing of one or more of the conduits may occur. Particles produced as a result of the fracturing may undesirably block the fluid path within the conduits.

SUMMARY OF THE INVENTION

In accordance with one aspect of the inventions is a connector for connecting a first conduit to a second conduit comprising: a body having a passageway therethrough, a first cavity being at a first end of the passageway and a second cavity at a second end of the passageway; a first sealing member for providing a substantially fluid tight seal for the first conduit; a second sealing member for providing a substantially fluid tight seal for the second conduit; a first compression fitting for compressing the first sealing member by applying forces to the first sealing member, the forces including a rotational force; a second compression fitting for compressing the second sealing member by applying forces to the second sealing member, the forces including a rotational force; a first set of one or more keys and one or more mated key ways for preventing rotation of the first conduit when the first sealing member is compressed; and a second set of one or more keys and one or more mated key ways for preventing rotation of the second conduit when the second sealing member is compressed, wherein each of the first cavity and the second cavity in the body is configured to receive one of the sealing members or a detachable holder configured to receive one of the sealing members. An embodiment of the connector may include a stop indicating an insertion point in the body for the conduits. The stop may be electrically conductive. An embodiment of the connector may include one or more keys in a sealing member and a detachable holder with one or more mated key ways. An embodiment may include one or more keys in a sealing member and one or more mated key ways in the body. An embodiment may include one or more mated key ways in a sealing member.

In accordance with another aspect of the invention is a method for connecting a first conduit to a second conduit comprising: providing a body having a passageway through the body, a first cavity being at a first end of the passageway and a second cavity at a second end of the passageway; providing a first sealing member with the first conduit inserted therethrough; providing a second sealing member with the second conduit inserted therethrough; inserting, directly or indirectly, a first sealing member into the first cavity;

inserting, directly or indirectly, a second sealing member into the second cavity; compressing the first sealing member with a first compression fitting, said compressing applying forces to the first sealing member to provide a substantially fluid tight seal for the first conduit, the forces including a rotational force, said compressing engaging a first set of one or more keys and one or more mated key ways preventing rotation of the first conduit when the first sealing member is compressed; and compressing the second sealing member with a second compression fitting, said compressing applying forces to the second sealing member to provide a substantially fluid tight seal for the second conduit, the forces including a rotational force, said compressing engaging a second set of one or more keys and one or more mated key ways preventing rotation of the second conduit when the second sealing member is compressed. An embodiment may use a stop or a positioning tool to position the conduits in the body. The stop and the body may be electrically conductive and included in an electrically conductive path to fluid passing between the conduits, and a voltage may be applied to the body.

In accordance with another aspect of the invention is a connector for connecting a first conduit to a second conduit comprising: a body having a passageway through the body, a first cavity being at a first end of the passageway and a second cavity at a second end of the passageway; a first sealing member providing a substantially fluid tight seal for the first conduit, said first cavity being configured to receive, directly or indirectly, said first sealing member, said first sealing member having the first conduit inserted therethrough; a second sealing member providing a substantially fluid tight seal for the second conduit, said second cavity being configured to receive, directly or indirectly, said second sealing member, said second sealing member having the second conduit inserted therethrough; a first compression fitting for compressing the first sealing member by applying forces to the first sealing member, the forces including a rotational force; a first set of one or more keys and one or more mated key ways which are engageable to prevent rotation of the first conduit when the first sealing member is compressed; a second compression fitting for compressing the second sealing member by applying forces to the second sealing member, the forces including a rotational force; and a second set of one or more keys and one or more mated key ways which are engageable to prevent rotation of the second conduit when the second sealing member is compressed.

In accordance with another aspect of the invention is a connector for connecting a first conduit to a second conduit comprising: a body having a passageway through the body, a first cavity being at a first end of the passageway and a second cavity at a second end of the passageway; a stop included in said body indicating an insertion point for the first conduit and the second conduit; a first elastomeric core portion in the first cavity for providing a substantially fluid tight seal between the first conduit, walls in the first cavity, and the stop, said first elastomeric core portion having the first conduit inserted therethrough; a second elastomeric core portion in the second cavity for providing a substantially fluid tight seal between the second conduit, walls in the second cavity, and the stop, said second elastomeric core portion having the second conduit inserted therethrough; a first compression fitting for compressing the first elastomeric core portion by applying forces to the first elastomeric core portion; and a second compression fitting for compressing the second elastomeric core portion by applying forces to the second elastomeric core portion.

In accordance with yet another aspect of the invention is a connector for connecting a first conduit to a second conduit comprising: a body having a passageway therethrough, a first cavity being at a first end of the passageway and a second cavity at a second end of the passageway; a first sealing member for providing a substantially fluid tight seal for the first conduit; a second sealing member for providing a substantially fluid tight seal for the second conduit; a first compression fitting for compressing the first sealing member by applying forces to the first sealing member; a second compression fitting for compressing the second sealing member by applying forces to the second sealing member; and a stop in the body indicating an insertion point in the body for the first conduit and the second conduit, wherein each of the first cavity and the second cavity in the body is configured to receive one of the sealing members or a detachable holder configured to receive one of the sealing members.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIGS. 4A-4F are examples of components that may be included in a third embodiment of a connector in accordance with the invention;

FIGS. 5A-5H are examples of components that may be included in a fourth embodiment of a connector in accordance with the invention;

FIGS. 7A-7G and 8A-8E are examples illustrating components that may be included in yet another embodiment of a connector in accordance with the invention;

FIGS. 8F-8G illustrate application of forces to components of a connector in accordance with the invention to provide a fluidic seal.

DESCRIPTION

The phrases "chromatographic system," "chromatographic module," "chromatographic instrument," and the like herein refer to equipment used to perform chemical separations. Such equipment is a portion of an instrument that includes other components or is a standalone unit. Chromatographic equipment typically moves fluids under pressure and/or electrical forces.

Depending on context, the description provided herein of some illustrative embodiments of the invention interchangeably uses the words "tube," "conduit," "capillary," and/or "pipe." Depending on context, the word "capillary" refers to fused-silica tubes and/or refers to relatively narrow tubes. Conduits may pass through an interior passageway such as may be formed, for example, by a bore, or hole extending through a ferrule.

Some embodiments of the invention involve instruments that include both chromatographic and mass-spectrometric components. In some of these embodiments, a chromatographic component is placed in fluid communication with a mass-spectrometric component through use of an appropriate interface, such as an electrospray-ionization interface. Some appropriate interfaces at times create or maintain separated materials in an ionic form and typically place a stream of fluid containing the ions into an atmosphere where the stream is vaporized and the ions are received in an orifice for mass-spectrometric analyses.

Figure 1A:
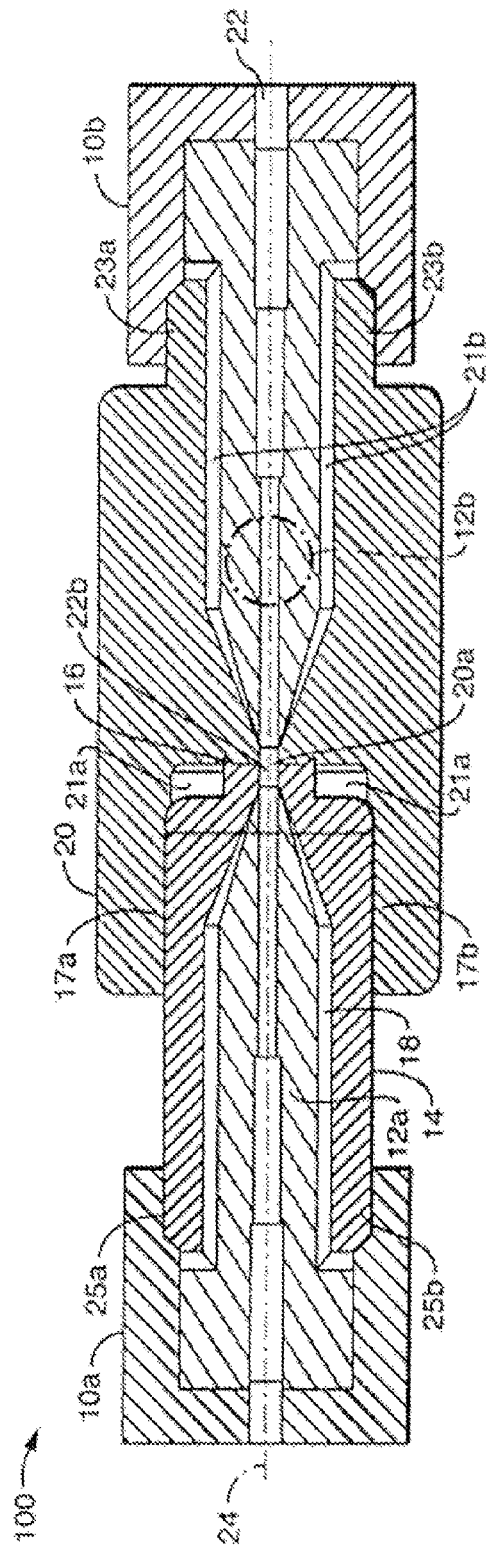
FIGS. 1A-1I, and 2A are examples of components that may be included in a first embodiment of a connector in accordance with the invention.

Referring to FIG. 1A, shown is an example illustrating a connector in accordance with one embodiment of the invention. The example 100 illustrates a cutaway view of the connector and includes compression fittings 10a, 10b, ferules 12a, 12b, a detachable ferrule holder 14, a stop 16, and a body 20. The connector 100 can be used to connect components that support the flow of a fluid, such as a liquid or a gas. The fluid can be a mixture, sample, material, and the like. The connector 100 can be used, for example, to connect a first conduit, such as a tube, to a second conduit, also a tube. A first conduit may be inserted into opening 22 of a bore through compression fitting 10b and through a bore in ferrule 12b to point 22b until the stop 16 is reached. The ferrule 12b may be inserted directly into a cavity 21b in the body 20 configured to receive the ferrule 12b. Thus, the cavity 21b in the body 20 which receives ferrule 12b serves as a ferrule holder which is incorporated or integrated into the body 20. In contrast, the detachable ferrule holder 14, as described below, provides for indirectly inserting and positioning the ferrule 12a into cavity 21a by first positioning the detachable ferrule holder in the cavity 21a and then positioning the ferrule 12a within the ferrule holder 14. As described in more detail herein, each of the ferrules may be used to provide a fluidic seal between a conduit and walls of the respective cavity into which each conduit is positioned.

The detachable ferrule holder 14 may be configured to receive the ferrule 12a, and the cavity 21a may be configured to receive the detachable ferrule holder 14. The detachable ferrule holder 14 may have a bore 15 extending through a wall of the holder 14 in an end opposite opening 24. The detachable ferrule holder 14 may be threaded on its outer surfaces 17a, 17b to mate with other threads on the inner surfaces of a cavity 21a in the body 20 into which the detachable ferrule holder 14 is inserted. A second conduit may be inserted into opening 24 of a bore through compression fitting 10a, through a bore in ferrule 12a, and through the bore 15 of the detachable ferrule holder 14 until the stop 16 is reached. A through hole 20a is formed in inner walls of the cavities 21a and 21b in the body 20 to connect 21a and 21b to facilitate a fluid path between the first and the second conduits. A passageway through the body 20 is formed by connected cavities 21a and 21b.

In the embodiment 100, the stop 16 functions as a mechanical stop to indicate an insertion point for the first and the second conduits. The stop 16 may be, for example, a disc approximating a round shape with a hole therethrough to allow for fluid passage between the first and second conduits. The hole in the disc serves as a fluidic port allowing for fluid passage has suitable dimensions selected in accordance with the dimensions of the conduits and other components of the connector. In order for the disc to function as a mechanical stop to indicate a point of insertion for the first conduit and the second conduit and also to allow for fluid passage therebetween, the hole in the disc has a diameter which is smaller than the outer diameter (OD) of the conduits. For example, a suitable measurement for the hole in the disc may be less than 50 um in diameter based on the particular dimensions of the conduits being connected. Other suitable dimensions may be selected for the disc or other component(s) functioning as the stop used in an embodiment.

The components in the example 100 are configured so that the compression fitting 10b, such as a threaded screw, can be tightened causing axial and rotational forces to be applied to the ferrule 12b causing the ferrule 12b to press against inner walls of the cavity 21b at a tapered end in a direction toward the disc causing the ferrule 12b to distort and compress around the conduit inserted therethrough. The outer surface areas 23a and 23b of the body 20 may include threads that are mated with threads on inner surfaces of compression fitting 10b. Further tightening of the compression fitting 10b will impart an axial compression on the ferrule 12b which, since prevented from expanding radially outwards by the inner walls of the cavity 21b in body 20, will compress radially inwards and against the first conduit providing a fluidic seal. The forces applied when the compression fitting 10b is tightened cause the first conduit inserted through ferrule 12b to move in a horizontal direction toward the disc until the first conduit is compressed against an exposed surface of the disc. The ferrule 12b is used to create a fluidic seal between the first conduit and the disc and between the first conduit and the inner walls of the cavity 21b in the body 20. In accordance with the embodiments described herein, the components included in the connector prevent the ferrules 12a, 12b from rotating as the foregoing forces are applied by tightening of the compression fittings 10a,10b. In the embodiment of the connector 100 as will be described in more detail in following paragraphs, the ferrule 12b, and similarly 12a, each includes a key portion. The key portion includes two keys configured to be received by corresponding key ways. In connection with the ferrule 12b in the embodiment of the connector 100 of FIG. 1A, the key ways are incorporated into the body 20. When the keys of the ferrule 12b are engaged within the keyways and a rotational force is applied thereto, the ferrule 12b, and the first conduit inserted therethrough, do not rotate. Thus, a fluidic seal may be applied to the OD of the first conduit inserted through the bore in ferrule 12b and the body 20 while preventing rotation of the first conduit. In connection with the ferrule 12a, the key ways are formed in the detachable ferrule holder 14 as described in more detail herein and prevent rotation of the conduit inserted through ferrule 12a in a manner similar to that as for ferrule 12b.

The ferrule 12b provides a seal between the first conduit and the inner walls of the cavity 21b of the body to prevent fluid leakage. With the detachable ferrule holder 14, the ferrule 12a is used in providing a fluidic seal between the second conduit and inner walls of cavity 18 of the ferrule holder into which the ferrule 12a is inserted and between the disc 16 and the second conduit. By tightening the compression fittings 10a, 10b, a leak resistance is obtainable. The compression fittings 10a, 10b can be tightened against the respective ferrules to provide a desired level of force application to the ferrule. A desired level of force can provide leak resistance up to a selected level of fluid pressure in accordance with the operating pressure of a system in which the techniques herein are utilized.

The ferrules 12a, 12b may be more generally characterized as deformable fittings. In embodiments described herein, a ferrule may be used as sealing member to provide a fluidic seal. Thus, ferrules are one example of sealing members. Other examples of sealing members are also described herein in connection with other embodiments. For convenience of description, some embodiments described herein use a sealing member which will be referred to herein as a "ferrule". It should be understood, however, that use of this term is not intended to limit embodiments of the invention to devices that include ferrule(s). Moreover, although the embodiments described herein include fittings that completely surround a conduit and have portions that form a continuous ring disposed around a conduit, alternative embodiments can include fittings that partially surround a conduit and/or only surround a conduit with a discontinuous ring. Furthermore, the term detachable ferrule holder is also used herein for convenience of description in connection with embodiments but may also be more generally referred to as a detachable holder.

Ferrule 12a includes a key portion with two keys configured to be received by key ways incorporated into the detachable ferrule holder 14 for purposes of preventing rotation of the ferrule 12a, and thus preventing rotation of the second conduit inserted through the bore in the ferrule 12a. In a manner similar to that as described for ferrule 12b, tightening of compression fitting 10a provides for creation of a fluidic seal to the OD of the second conduit inserted in ferrule 12a. The outer surface areas 25a and 25b of the detachable ferrule holder 14 may include threads that are mated with threads in an inner surface of compression fitting 10a.

The components of the connector in 100, as well as other embodiments of connectors described herein, may be fabricated from any suitable materials. For example, the ferrules 12a, 12b may be made of any suitably deformable material such as a polymer including any suitable polymers known to those skilled in the art. As an example, the ferrules 12a, 12b may be made from PEEK (polyether-ether-ketone) or steel. The compression fittings 10, 10b, body 20, and detachable ferrule holder 14 are formed of suitable material(s). Some suitable materials include metals, such as steel or other alloys, polymers, and/or ceramics. The body 20 may be electrically conductive and formed from suitable materials to provide the desired conductance. For example, the body 20 may be made from steel or other metal(s), carbon-filled PEEK, and the like. The components optionally include, for example, layers and/or mixtures of materials, and/or coatings. Such coating may provide for the desired electrical conductance. The conduits may be made from any suitable material such as fused silica, PEEK, steel, and the like, in accordance with the particular system and usage. The conduit(s) may be coated, for example as with fused silica to allow for flexibility. Each of the conduits may be made of the same or different materials.

The components of the connector of FIG. 1A, as well as other embodiments of connectors described herein, may be produced using any suitable production technique. For example, the components may be machined, produced using a mold, and/or using other suitable techniques known in the art for the selected materials. Depending on the size of the components and openings therein, openings may be produced using a laser or other suitable techniques.

Figure 1B:
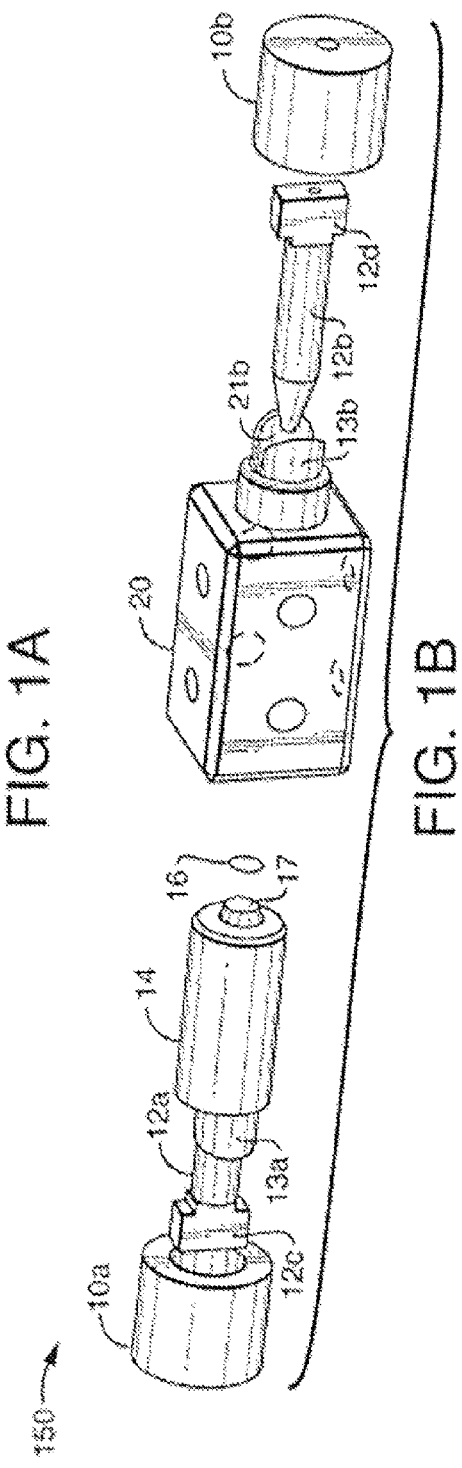

Referring to FIG. 1B, shown is a three-dimensional view of the connector of FIG. 1A shown prior to assembly (or after disassembly). One way in which the components of the connector illustrated in FIGS. 1A and 1B may be assembled will now be described. A first conduit may be inserted in a bore through ferrule 12b. A second conduit may be inserted in a bore through ferrule 12a. An outward surface at an end 17 of the detachable ferrule holder 14 may be configured to receive the disc 16. For example, the outward surface may include a raised circular lip extending a circumference about the center x-axis of the detachable holder 14 so as to form a circle with a diameter selected to be slightly larger than that of the OD of the disc. The holder 14 may be held at an orientation so that the end 17 extends upward at a sufficient angle with respect to the horizon and disc 16 is placed thereon. With the disc 16 at end 17 of the holder 14, the holder is then inserted into cavity 21a of the body 20 by tightening the detachable ferrule holder 14 and engaging the mated threads of the outer surface 17a, 17b of the holder and the inner surface of the cavity 21a. The body 20 and the detachable ferrule holder 14 are configured so that tightening the detachable ferrule holder 14 places the detachable holder 14 into position in the body 20. Additionally, tightening of the detachable holder 14 results in the disc 16 being held in its desired position within the body 20 since the disc 16 is compressed between the detachable ferrule holder 14 and an inner wall of the cavity 21a in contact with the inserted disc 16. Ferrule 12a may be placed into the detachable ferrule holder 14 so that the keys of the key portion 12c are positioned in the mated key ways of the detachable ferrule holder 14. Compression fitting 10a may then be tightened so as to compress ferrule 12a and position the second conduit passing through 12a in the body.

The ferrules 12a, 12b may be characterized as keyed ferrules. In the example 150, ferrule 12a includes key portion 12c and ferrule 12b includes key portion 12d. Each portion 12c, 12d in this example includes two keys. The keys can vary in shape from what is described herein and are not restricted to the squared off shape shown herein. The keys may be any shape which facilitates preventing the ferrule from rotating. For example, the keys may have more rounded edges. In this example, the ferrules 12a and 12b may be constructed to include similar key portions and keys so that the ferrules may be used interchangeably in an embodiment of the connector of FIG. 1A.

Compression fitting 10a may be tightened as described above so that an end of the second conduit in ferrule 12a is compressed against a surface of the disc 16. When compression fitting 10a is tightened, the ferrule 12a in the detachable ferrule holder is prevented from rotating by positioning keys of key portion 12c within key ways formed at end 13a of the detachable ferrule holder 14 as described in more detail in following paragraphs in connection with additional figures.

The ferrule 12b may be inserted into cavity 21b of body 20 and compression fitting 10b may be tightened as described above so that an end of the first conduit is compressed against a surface of the disc 16. Ferrule 12b may be positioned in the cavity 21b so that the keys of the key portion 12d are positioned in the mated key ways formed at end 13b of the body. When compression fitting 10b is tightened, the ferrule 12b is prevented from rotating by positioning keys of key portion 12d within key ways formed at end 13b of the body 20 as described in more detail in following paragraphs in connection with additional figures. In the embodiment of FIGS. 1A, 1B, the two key ways formed in the detachable ferrule holder 14 are diametrically opposed to one another. Similarly, the two key ways formed in the body 20 are also diametrically opposed to one another.

Figure 1C:
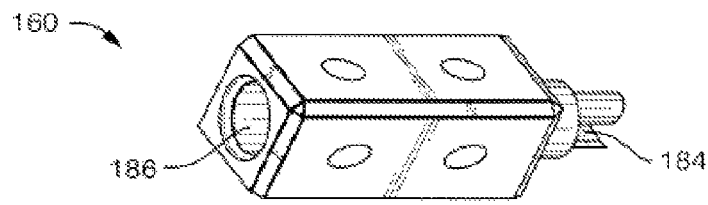
Figure 1D:
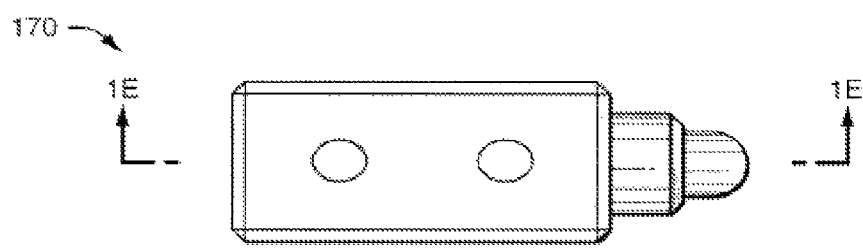
Figure 1E:
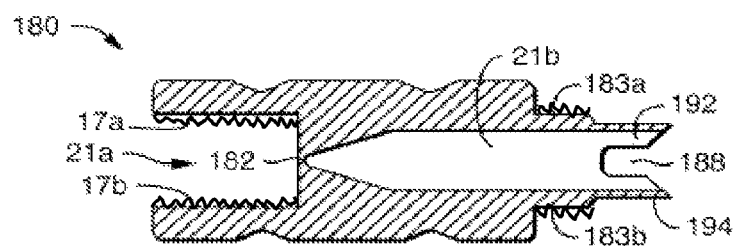
Figure 1F:
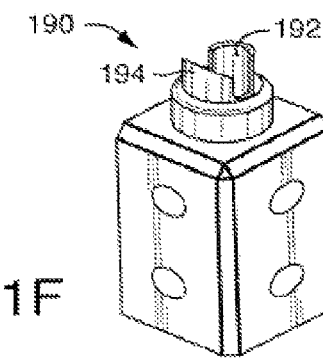

Referring to FIGS. 1C, 1D, 1E and 1F, shown are different views of the body of the connector of FIG. 1A in accordance with one embodiment of the invention. FIG. 1C illustrates key way 184 configured to receive a key of key portion 12d of the ferrule 12b. Element 186 illustrates an opening to cavity 21a into which the detachable ferrule holder 14 is inserted. FIG. 1D illustrates a side view and FIG. 1E represents a lateral cross-sectional view taken along 1E-1E as indicated in FIG. 1D. Element 182 illustrates the inner wall of the cavity 21a into which the disc 16 and detachable ferrule holder 14 are inserted as described above so that the disc 16 is flush against the wall 182. A through hole exists in wall 182 connecting cavities 21a and 21b. Elements 17a, 17b represent threaded inner surfaces that mate with threaded outer surfaces of the detachable ferrule holder. Elements 183a, 183b represent threaded outer surfaces that mate with threaded inner surfaces of the compression fitting. From the view in FIG. 1E, element 188 represents the two diametrically opposed key ways formed. When the keys of the ferrule are inserted into keyways 188, the ferrule is prevented from rotating when a rotational force is applied thereto. FIG. 1F illustrates the two key ways formed from two lip portions 192 and 194. The key ways are configured to receive keys of key portion 12d of ferrule 12b (as illustrated in FIG. 1B). The keyways in this embodiment are grooves formed by the two lip portions 192, 194 extending from the body.

In connection with the first, and other embodiments described herein, two key ways are formed by lip portions so that the key ways are diametrically opposed to one another. Other configurations having a different number and/or positioning of key ways are possible and may vary with the mated keys.

In connection with FIG. 1E, it should be noted that the cavity 21b includes a tapered end in accordance with the shape of the ferrule. As will be appreciated by those skilled in the art, the shape and dimensions of the interior of 21b may be determined in accordance with the shape and dimensions of the ferrule used in an embodiment. For example, a suitable angle for the tapered end is 40 degrees for the particular ferrule used. It should be noted that although the ferrule illustrated is tapered, an embodiment may also use a ferrule which has a different shape and/or is not tapered. In such a case, the cavities of the body and detachable ferrule holder may be suitably configured in accordance with the physical aspects of the ferrule utilized.

Figure 1G:
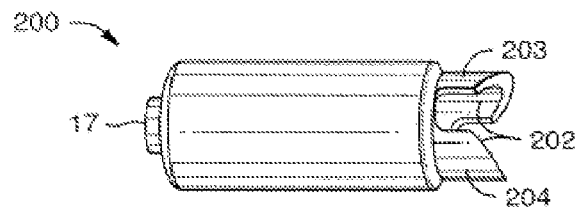
Figure 1H:
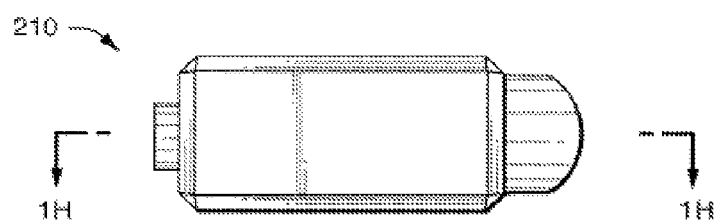
Figure 1I:
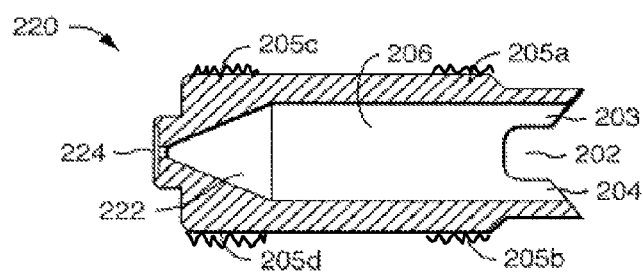

Referring to FIGS. 1G, 1H and 1I, shown are additional views of the detachable ferrule holder of the connector of FIG. 1A in accordance with one embodiment of the invention. FIG. 1G illustrates the lip portions 203 and 204 of the detachable ferrule holder that form the two diametrically opposed key ways 202 configured to receive the keys of key portion 12c of the ferrule 12a illustrated in FIG. 1B. The end portion 17 is shown which may be configured to receive the disc in this embodiment. FIG. 1H shows a side view of the detachable ferrule holder with one of lip portions 202, 204 facing outward. FIG. 1I shows a lateral cross-sectional view taken along lines 1H-1H of FIG. 1H. FIG. 1I illustrates another view of the lip portions 203 and 204 forming key ways 202. As with cavity 21b of the body described above, the cavity 206 of the detachable ferrule holder which also receives a ferrule has shape and dimensions determined in accordance with the ferrule used in an embodiment. For example, the cavity 206 includes tapered portion 222 in accordance with the shape of the ferrule used in the exemplary embodiment herein. Element 224 illustrates the opening formed through the wall of the detachable ferrule holder to facilitate a passage for the fluid path between the first and second conduits. With reference back to FIG. 1A, the detachable ferrule holder and body are configured so that the opening 224 is axially and radially aligned with the through hole 20a connecting cavities 21a and 21b of the body. Elements 205a, 205b, 205c and 205d identify outer surface areas of the detachable ferrule holder which may include threaded portions. Elements 205c and 205d illustrate areas of threaded portions mated with threads on the inner surface of the body 20 of FIG. 1A, 1B. Elements 205a and 205b illustrate areas of threaded portions mated with threads on the inner surface of the compression fitting, such as 10a of FIG. 1B.

As described in connection with key ways formed in the body for the first, and other embodiments described herein, two key ways are formed by lip portions so that the key ways which are diametrically opposed to one another. Other configurations having a different number and/or positioning of key ways are possible and may vary with the mated keys.

It should be noted that the key way described herein for purposes of illustration in this and other embodiments may be characterized as a groove formed by lip portions. As will be appreciated by those skilled in the art, different key ways may be formed in accordance with the particulars of the keys used in an embodiment. For example, the key way may be formed using one or more holes having a corresponding key which is a pin or other item inserted into one of the holes.

As just described and referring back to FIG. 1A, a first end of the detachable ferrule holder 14 may be engageable with the body 20 and a second end of the detachable holder 14 may also be engageable with the compression fitting 10a. A compression fitting may be engageable with the body 20, as in the case where the ferrule 12b is directly in the cavity 21b of the body 20. The compression fitting may also be engageable with the detachable ferrule holder 14, as in the case where the ferrule 12a is in detachable ferrule holder 14. One embodiment of the compression fitting may be engagable with both the detachable holder 14 and the body 20 using the same threaded portion of the compression fitting so that the same compression fitting can be used interchangeably with the detachabled holder 14 and the body 20. The detachable ferrule holder 14 is engaged with the body 20 to position the detachable holder 14 in the cavity 21a of the body. The detachable ferrule holder 14 may be positioned and secured in a desired position within the cavity 21a as by tightening the detachable holder 14 against the body 20 using mated threaded portions. The conduit inserted through the ferrule 12a may be positioned and secured in a desired position in the body 20 as by tightening the compression fitting 10a against the detachable holder 14 using mated threaded portions. The conduit inserted through ferrule 12b may be positioned and secured in a desired position in the body 20 as by tightening the compression fitting 10b against the body 20 using mated threaded portions. The foregoing applies to components as just described in connection with the first embodiment of the connector as well as others described herein. In the first embodiment and others described herein, the disc may be used to indicate the insertion point in the body for the first and second conduits. The axial movement of the conduits toward each other in the body 20 due to compression by respective compression fittings passed a desired insertion point is prevented by the disc that serves as a mechanical stop located at the desired insertion point in the body 20. Other suitable means may be used to position the conduits in the body in accordance with a desired insertion point, such as with the use of a positioning tool also described herein in connection with other embodiments.

Figure 2A:
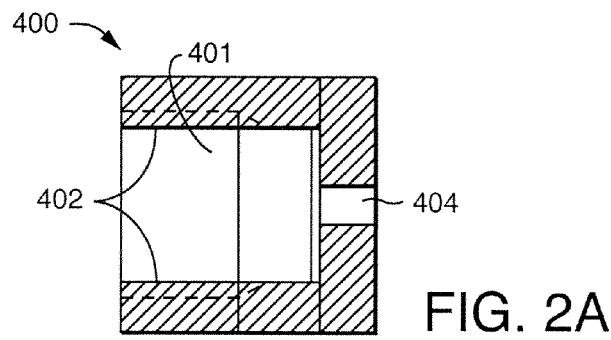

Referring to FIG. 2A, shown is a cutaway view of the compression fittings 10a and 10b as may be included in a connector in accordance with an embodiment of the invention. The example 400 illustrates a compression fitting that may be a compression screw with threaded portions 402 formed on inner surfaces of a cavity 401 of the fitting. Element 404 illustrates a hole through an inner wall at an end of the cavity 401 through which the conduit passes. In an embodiment, each of the compression fittings 10a, 10b may be as illustrated in FIG. 2A so that the threaded inner surfaces 402 are configured with mated threaded portions of both the detachable ferrule holder 14 (e.g., 205a, b of FIG. 1I) and the body 20 (e.g., 183a, 183b of FIG. 1E). It should be noted that an embodiment may configure a compression fitting so as to engagable with the body and/or the detachable holder. The compression fitting of FIG. 2A may be used in connection with compression fittings for other embodiments described herein.

Figure 2B:
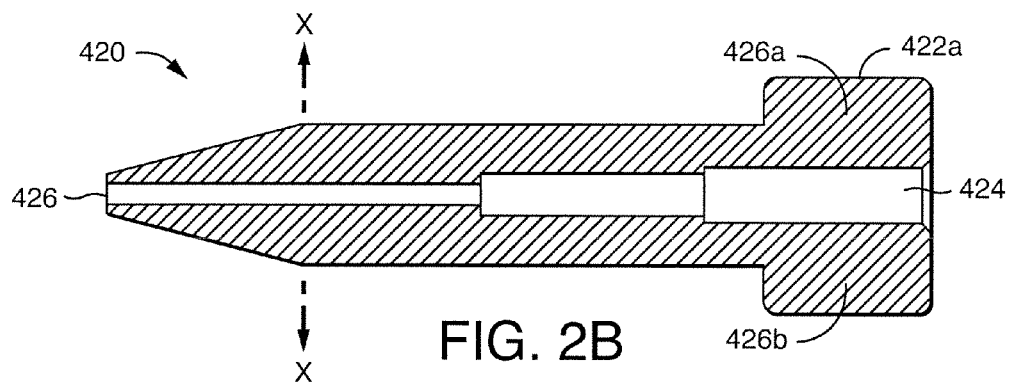
FIGS. 2B-2D, and 3I are examples of different views of ferrules that may be included in an embodiment in accordance with the invention.
Figure 2C:
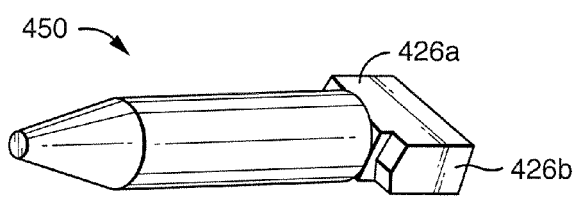
Figure 2D:
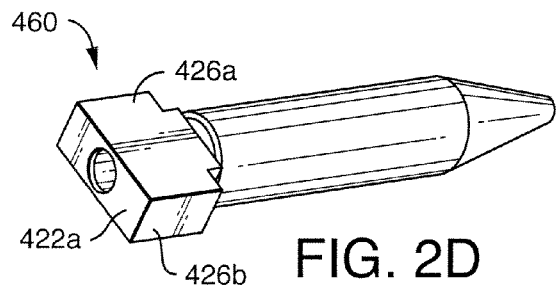
Figure 2E:
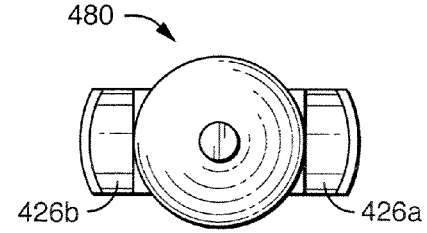

Referring to FIG. 2B, shown is a cutaway view of the ferrules 12a, 12b in accordance with an embodiment of the invention. The ferrule 420 includes a bore therethrough with openings 424 and 426 at opposing ends of the ferrule through which the conduit passes. Element 422a illustrates a key portion of the ferrule formed by keys or extensions 426a and 426b. The ferrule includes a tapered end which is at an end opposite the key portion. The outer surface of the ferrule at opening 426 may be compressed against a surface of the disc when assembled. FIGS. 2C, 2D and 2E illustrate other views of the ferrule that may be included in a connector in accordance with an embodiment of the invention. In this example, the bore through the ferrule consists of a series of graduated diameters with the tapered end having the smallest of such diameters. However, as will be appreciated by those skilled in the art, the ferrule may include a bore configured with other variations. Another example of a ferrule that may be used in an embodiment is described elsewhere herein in FIG. 3I.

It should be noted that the ferrule included herein for purposes of illustration includes two keys. However, it will be appreciated by those skilled in the art that the ferrule may generally include one or more keys with a key way accordingly configured.

The disc used as a stop to position the conduits within the body of the connector has been illustrated as being a separate component. However, in the embodiments described herein, the disc may alternatively formed as an integral part of another component rather than as a separate component. For example, the disc may be formed as an integral part of the body, or as an integral part of the ferrule holder using suitable fabrication techniques.

In connection with the embodiment described, keys and mated key ways configured to receive the keys are used to prevent rotation of the ferrule, and thus prevent rotation of the conduit extending through the ferrule. The embodiment just described incorporates the keys in the ferrule. In the case of a detachable ferrule holder used with the ferrule, the key ways are formed using the detachable ferrule holder. In the case where the ferrule is inserted directly into the body so that the ferrule holder is incorporated into the body, the key ways are formed using the body. The embodiment of the connector just described uses a single detachable ferrule holder. As described below in connection with other embodiments in accordance with the invention, the connector may utilize two detachable ferrule holders or no detachable ferrule holders. Furthermore, an embodiment may also use different features of the connector in providing the keys and key ways to prevent rotation of the ferrule, and thus, prevent rotation of the conduit inserted therethrough.

Figure 3A:
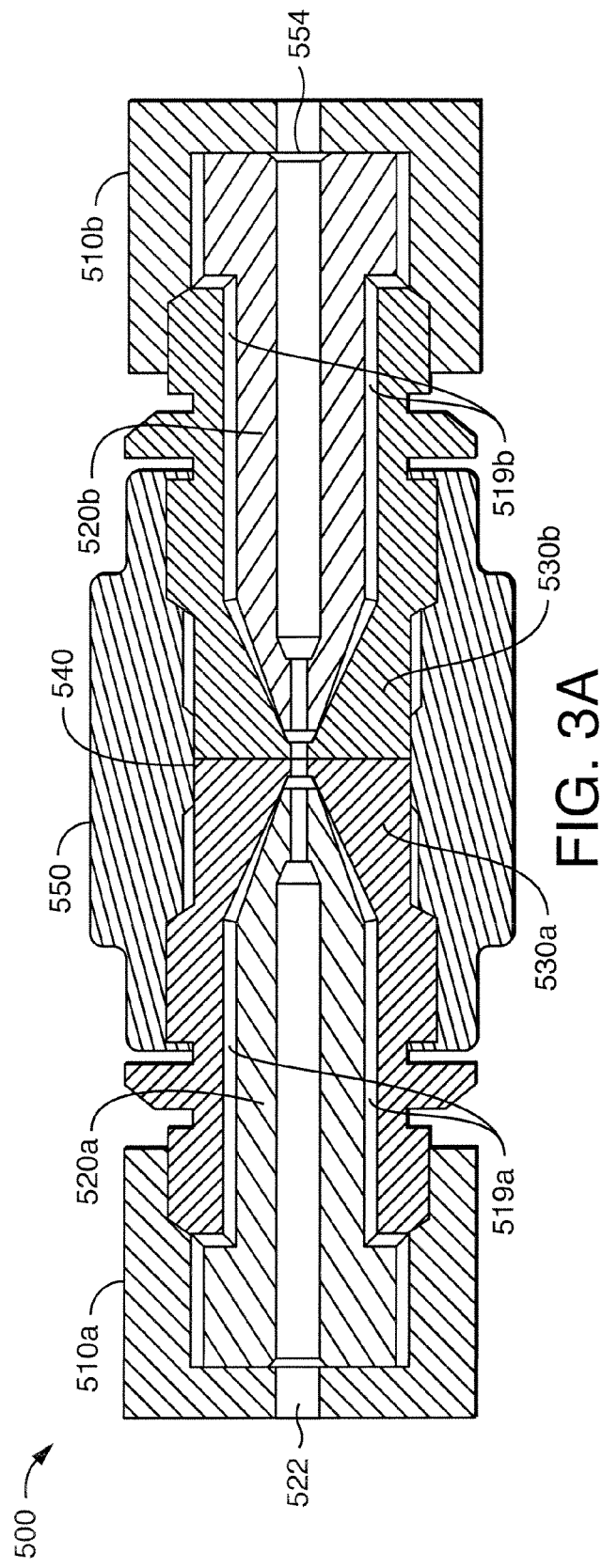
FIGS. 3A-3H are examples of components that may be included in a second embodiment of a connector in accordance with the invention.

Referring to FIG. 3A, shown is an example illustrating a connector in accordance with another embodiment of the invention. The example 500 illustrates a cutaway view of the connector and includes compression fittings 510a, 510b, ferrules 520a, 520b, detachable ferrule holders 530a, 530b, a stop 540, and a body 550. The body 550 includes connected cavities 519a, 519b into which the detachable ferrule holders are positioned. An interior passageway is formed through the body 550 by connected cavities 519a, 519b. Components of this second embodiment are similar to as described above in connection with the first embodiment as described in connection with FIGS. 1A and 1B. The first embodiment includes a connector having a single detachable ferrule holder and utilizes a second ferrule holder incorporated as an integral part of the body. In the second embodiment illustrated in FIG. 3A, two detachable ferrule holders are included in the connector. Both the detachable ferrule holders 530a operate as described in the first embodiment. Rotation of the ferrules 520a and 520b, and thus the conduits inserted therethrough, is prevented by keys of the ferrules and mated key ways formed in the detachable ferrule holders. As with the first embodiment, the key ways of the detachable ferrule holders in the second embodiment are diametrically opposed to one another.

The second embodiment also utilizes a stop 540, such as a disc, functioning as a mechanical stop to allow for desired positioning of the two conduits being connected within the body 550. The disc 540 may rest in its desired position in the body 520 when both detachable ferrule holders are in position, such as after the compression fittings 510a, 510b have been tightened. As an example, the connector in the second embodiment may be assembled by inserting each of the conduits through a bore in one of the ferrules 520a, 520b. A first detachable ferrule holder may be inserted into position in the body 550 in one of the cavities 519a, 519b of the body as by tightening of the first detachable ferrule holder so as to engage the threaded portions on the inner surface of the body 550 and the outer surface of the first detachable ferrule holder. Then, as described in connection with the first embodiment, the disc may be placed on an end of the second detachable ferrule holder. Alternatively, the body may be held in a position which is approximately perpendicular with respect to that illustrated in FIG. 3A and the disc may be dropped into the cavity other one of the cavities 519a, 519b. The second detachable ferrule holder may be inserted into position in the body 550 in the other one of the cavities 519a, 519b as by tightening the second detachable ferrule holder. Each of the ferrules 520a and 520b may be positioned in one of the detachable ferrule holders 530a, 530b by tightening the compression fittings 510a, 510b as described above. Prior to tightening the compression fitting 510a, 510b, the keys of the ferrules 520a, 520b are positioned in their respective key ways formed in the detachable ferrule holders 530a, 530b. As with the detachable ferrule holder 14 of the first embodiment, when the compression fittings 510a, 510b are tightened, the keys positioned in the mated key ways of the detachable ferrule holders prevent the ferrules 520a, 520b from rotating. Other variations to the foregoing method of assembly are possible and may vary in accordance with the particular design of the components.

Figure 3B:
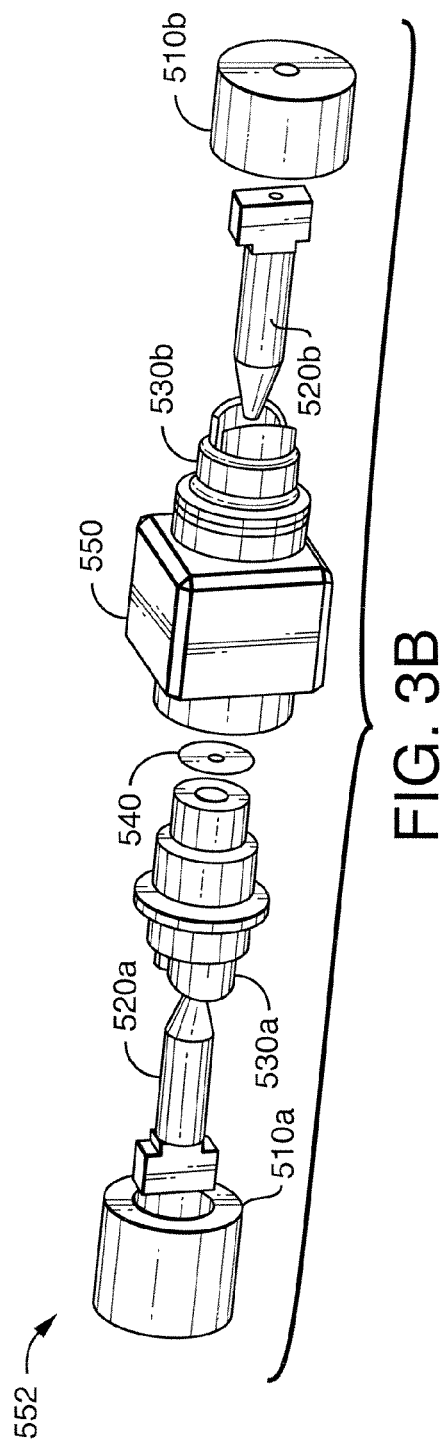

Referring to FIG. 3B, shown is a three-dimensional view of the connector of FIG. 3A shown prior to assembly (or after disassembly).

Figure 3C:
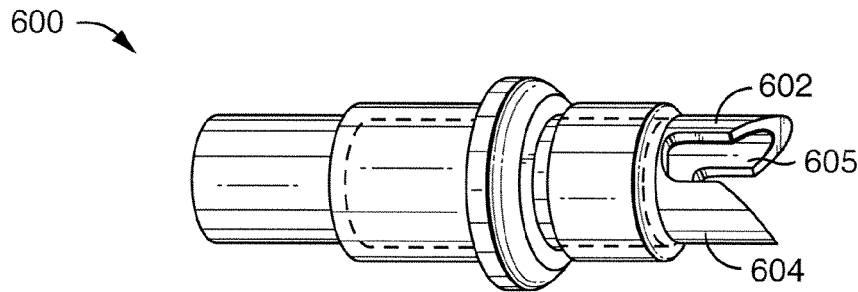
Figure 3D:
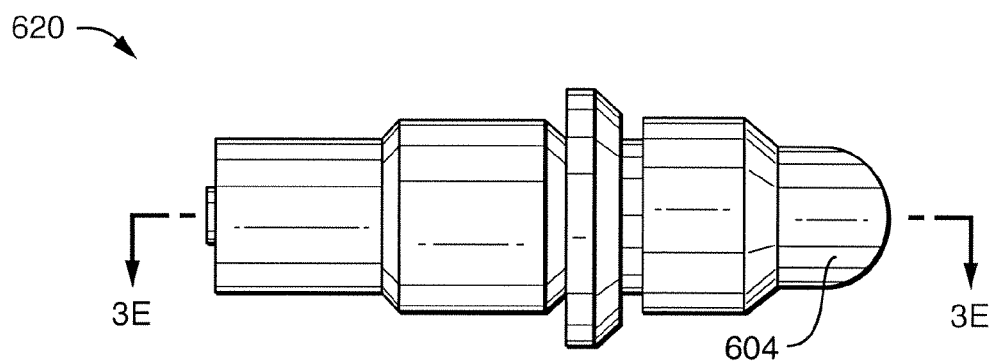
Figure 3E:
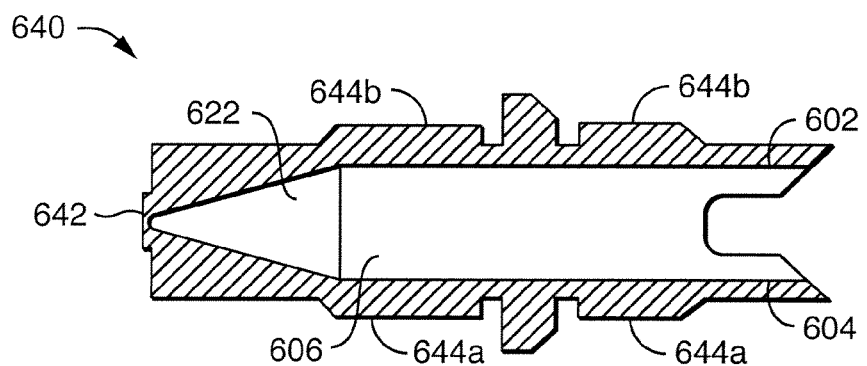

Referring to FIGS. 3C, 3D and 3E, shown are additional views of the detachable ferrule holder of the connector of FIG. 3A,3B in accordance with an embodiment of the invention. FIG. 3C illustrates the lip portions 602, 604 of the detachable ferrule holder that form the two key ways 605 configured to receive the two keys of a ferrule. FIG. 3D shows a side view of the detachable ferrule holder with one of lip portions 602, 604 facing. FIG. 3E shows a lateral cross-sectional view taken along lines 3E-3E of FIG. 3D. As described in connection with the detachable ferrule holder 14 of the first embodiment, the cavity 606 of the detachable ferrule holder which receives a ferrule has shape and dimensions determined in accordance with the ferrule used in an embodiment. For example, the cavity 606 includes tapered end portion 622 in accordance with the shape of the ferrule used in the exemplary embodiment herein. Element 642 illustrates the opening formed through the wall of the detachable ferrule holder to facilitate a passage for the fluid path between the first and second conduits. Elements 644a, 644b refer to outer surfaces of the detachable ferrule holder including threaded portions mated with threads on inner surfaces of the compression fitting (as illustrated, for example, in FIG. 2E) and body (as illustrated, for example, in FIG. 3H).

Figure 3F:
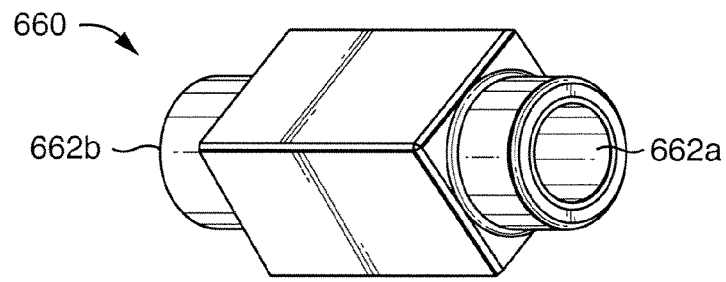
Figure 3G:
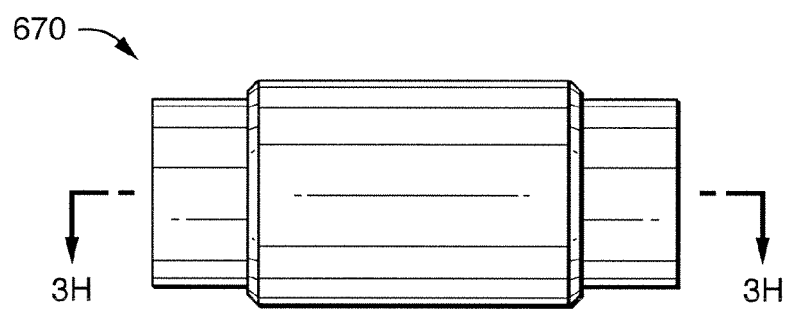
Figure 3H:
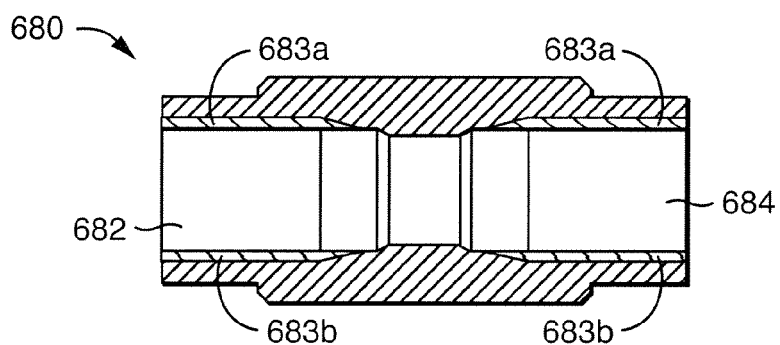

Referring to FIGS. 3F, 3G and 3H, shown are different views of the body of the connector of FIGS. 3A, 3B in accordance with one embodiment of the invention. FIG. 3F includes openings 662a, 662b into which the detachable ferrule holders are inserted. FIG. 3G illustrates a side view and FIG. 3H represents a lateral cross-sectional view taken along 3H-3H as indicated in FIG. 3D. Elements 683a, 683b refer to inner surfaces of the body cavities 682, 684 that include threaded portions mated for threads included in the outer surfaces of the detachable ferrule holders.

It should be noted that in connection with the foregoing second embodiment of the connector, fluidic seals are created in a manner similar to that as described in connection with the conduit 12a of FIG. 1A when ferrule holder 14 is used.

Figure 3I:
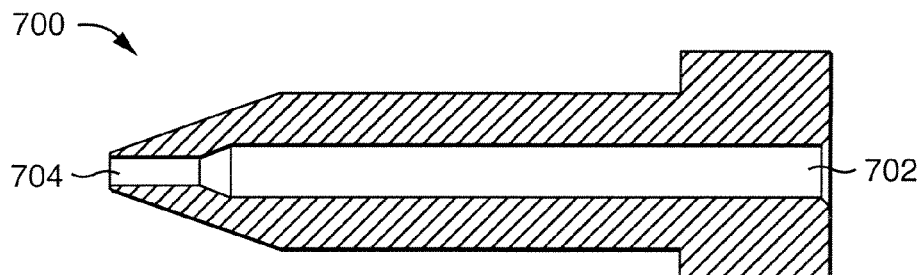

Referring to FIG. 3I, shown is a cutaway view of the ferrules 520a, 520b as may be included in a connector in accordance with an embodiment of the invention. The ferrule 700 includes a bore therethrough with openings 702 and 704 at opposing ends of the ferrule through which the conduit passes. The ferrule 700 is similar to that as described in connection with FIG. 2B with a difference being the shape and dimension of the bore through the ferrule through which the conduit passes.

It should be noted that either of the embodiments of the ferrules as illustrated in FIGS. 2B and 3I may be used in connection with any of the embodiments of the connector described herein which uses ferrules.

Referring to FIG. 4A, shown is an example illustrating a connector in accordance with another embodiment of the invention. The example 850 illustrates a cutaway view of the connector and includes compression fittings 802a, 802b, ferrules 804a, 804b, and a body 806. Components of this third embodiment are similar to those as described above in connection with the first embodiment as described in connection with FIGS. 1A and 1B. The first embodiment includes a connector having a single detachable ferrule holder and utilizes a second ferrule holder which is incorporated as an integral part of the body. In the third embodiment illustrated in FIG. 4A, the two ferrule holders are incorporated as an integral part of the body of the connector so that the ferrules 804a, 804b are inserted directly into the body 806. Rotation of the ferrules 804a, 804b, and thus the conduits inserted therethrough, is prevented by engaging keys of the ferrules with mated key ways formed in the body 806. Ferrules 804a and 804b may be positioned in the body 806 in a manner similar to that as described in connection with ferrule 12b of FIGS. 1A, 1B illustrating the first embodiment of the connector. The body 806 has a passageway formed therethrough by cavities 812a, 812b, and bore 810 connecting 812a and 812b. As described above in connection with the exemplary first and second embodiments, the key ways in the third embodiment are diametrically opposed to one another.

The third embodiment does not, however, utilize a stop, such as a disc as in connection with the first and second embodiments. As an alternative, a positioning tool may be utilized to position the conduits within the body 806. An exemplary illustration of a positioning tool that may be used is described elsewhere herein in more detail.

Figure 6A:
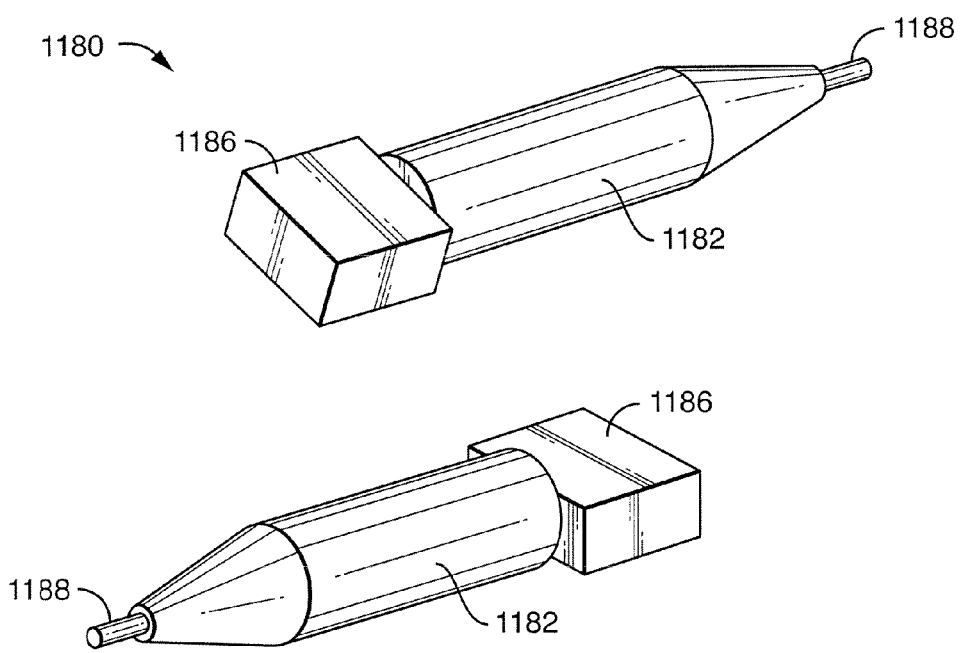
FIG. 6A is an example illustrating a positioning tool that may be used in connection with embodiments of a connector in accordance with the invention.

Referring to FIG. 6A, shown is an illustration of a positioning tool that may be used in an embodiment to position conduits within a connector. The positioning tool 1180 may be used in connection with the third embodiment of the connector of FIGS. 3A and 3B. The positioning tool 1180 includes features similar to that of the keyed ferrules with an elongated tip portion 1188 at a tapered end of the tool. Additionally, the tool 1180 does not require a bore to be formed therethrough. The length of the top portion 1188 is in accordance with the desired position of the conduits within the body and the length of 810 of FIG. 4A. The positioning tool 1180 illustrated includes a key portion 1186. However, the tool 1180 does not have to include a key portion as needed for preventing rotation of the ferrule. However, an embodiment of the tool may include the key portion 1186 having this or another form. The key portion 1186 may be used to facilitate insertion and removal of the tool 1180 from the body of the connector as described below in connection with positioning the conduits.

The positioning tool may be formed from suitable materials, for example, such as those described herein in connection with the ferrules.

With reference back to FIG. 4A, the connector in the third embodiment may be assembled using the positioning tool of FIG. 6A as will now be described. The positioning tool is inserted into a first one of the cavities 812a, 812b of the body 810 and the compression fitting is tightened to position the tool in the body. A first ferrule with a first conduit therethrough is then inserted into the body 810 into the other one of cavities 812a, 812b. The compression fitting used with the other cavity is tightened to position the first conduit. As the compression fitting used with the other cavity is tightened, an end of first conduit is compressed against an end of the tip portion 1188 of the positioning tool within the body 806. The positioning tool is then removed from the body 806 as by untightening the corresponding compression fitting. The second ferrule and second conduit therethrough are then inserted into the first of the cavities 812a, 812b. The second conduit is positioned within the body 806 by tightening the compression fitting for the first cavity. An end of the second conduit extending from the tapered end of the second ferrule into the body 806 is compressed against the end of the first conduit previously compressed against the tip portion 1188 of the positioning tool.

The third embodiment of the connector illustrated in FIG. 3A may utilize a keyed ferrule as described, for example, in connection with FIG. 3I or FIG. 2B. As in the first embodiment in connection with ferrule 12b being positioned in the body 20, the keys of ferrules 804a, 804b may be positioned in the keyways of the body 806 so that rotation of the ferrules 804a, 804b is prevented as the compression fittings 802a, 802b are tightened.

Referring to FIG. 4B, shown is a three-dimensional view of the connector of FIG. 4A shown prior to assembly (or after disassembly).

Figure 4C:
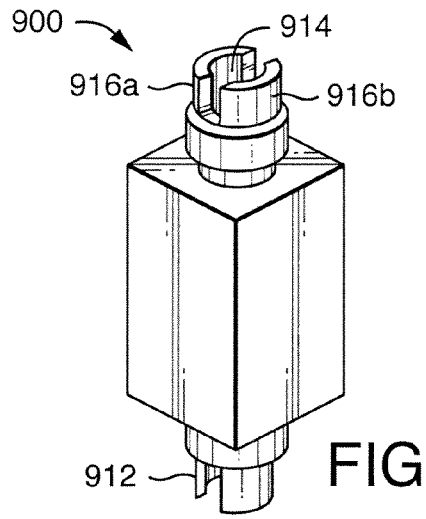
Figure 4D:
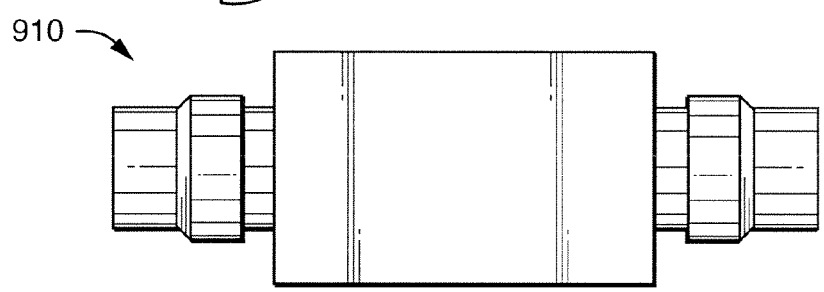
Figure 4E:
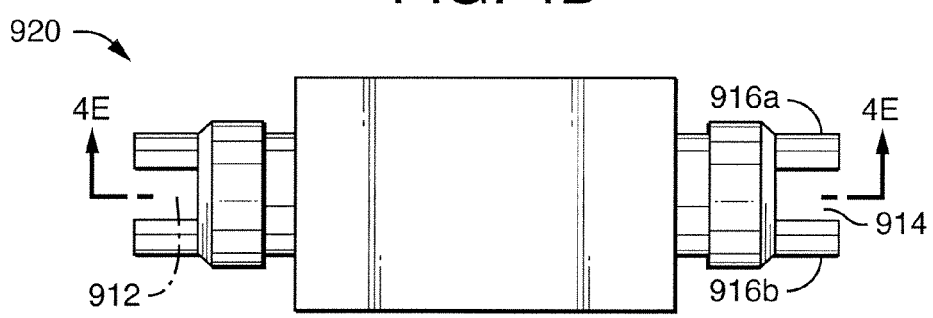
Figure 4F:
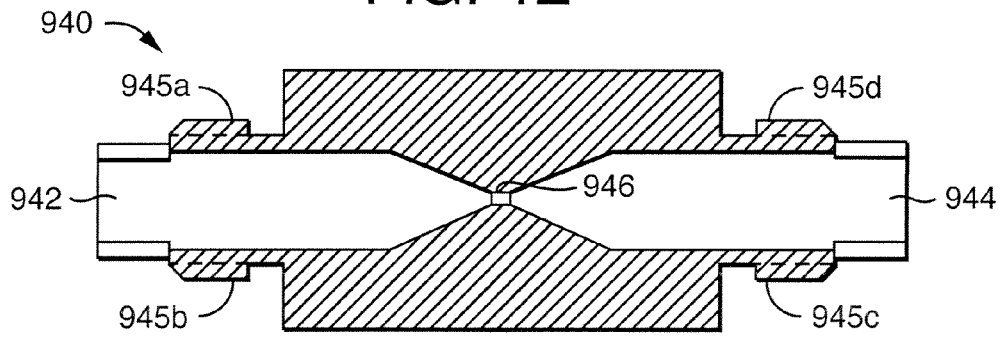

Referring to FIGS. 4C, 4D, 4E and 4F, shown are different views of the body 806 of the connector of FIGS. 4A, 4B in accordance with an embodiment of the invention. FIG. 4C illustrates key ways 912 and 914 configured to receive the keys of the ferrules 804a, 804b of FIG. 4A, 4B. Elements 916a, 916b illustrate the lip portions forming the two key ways 914 at one end of the body. It should be noted that the view of FIG. 4C does not show both diametrically opposed grooves of 912 located at the opposite end of the body. FIG. 4D illustrates a side view of the body 806 with one of the lip portions 916a, 916b facing. FIG. 4E is another side view of the body in which the body is rotated 90 degrees about its x-axis with respect to the view of FIG. 4D. Elements 916a, 916b are lip portions forming two diametrically opposed key ways 914. FIG. 4F represents a lateral cross-sectional view taken along 4E-4E as indicated in FIG. 4D. Elements 945a-945d represent portions of threaded outer surfaces which mate with threaded inner surfaces of compression fittings, such as illustrated in FIG. 2A.

The ferrules used in connection with the first and second embodiments described herein may be used with the third embodiment.

What will now be described is a fourth embodiment of a connector utilizing a different key and associated key way.

Referring to FIG. 5A, shown is an example illustrating a connector in accordance with another embodiment of the invention. The example 1050 illustrates a cutaway view of a fourth embodiment of the connector and includes compression fittings 1002a, 1002b, ferrules 1004a, 1004b, and a body 1006. Components of this fourth embodiment are similar to as described above in connection with other embodiments. For example, the third embodiment as described in connection with FIGS. 4A and 4B includes a connector having two ferrule holders incorporated as an integral part of the body of the connector so that the ferrules are inserted directly into the body. Similarly, the fourth embodiment of FIG. 5A also includes two ferrule holders which are an integral part of the body of the connector. The body 1006 has a passageway formed therethrough by cavities 1052a, 1052b, and bore 1007 connecting 1052a and 1052b.

The fourth embodiment does not, however, utilize a stop, such as a disc as in connection with the first and second embodiments. As an alternative, a positioning tool may be utilized to position the conduits within the body 1006 in a manner similar to that as described in connection with the third embodiment.

In contrast to the previous 3 embodiments described herein, the fourth embodiment uses a different key and key way. In particular, the fourth embodiment does not utilize a keyed ferrule. The key and key way in the fourth embodiment of the connector is described in more detail below.

Referring to FIG. 5B, shown is a three-dimensional view of the connector of FIG. 5A shown prior to assembly (or after disassembly). The example 1000 of FIG. 5B illustrates in more detail the ferrules 1004a and 1004b and the body 1006. As will be apparent from figures and description, the fourth embodiment utilizes ferrules 1004a and 1004b which may also be characterized as non-keyed ferrules since the ferrules 1004a, 1004b do not include features operating as the keys. Ferrule 1004a includes a first groove 1005a and a second groove (not illustrated) formed on an outer surface of the ferrule 1004a at a location that is diametrically opposed to groove 1005a. Similarly, ferrule 1004b includes a first groove 1005b and a second groove (not illustrated) formed on an outer surface of ferrule 1004b at a location that is diametrically opposed to groove 1005b. The grooves 1005a, 1005b, and two respective diametrically opposed grooves serve as key ways in the fourth embodiment. The body 1006 includes a hole 1009b formed through a wall of the sleeve 1011b of the body. A second hole (not illustrated) is also formed through the wall of the sleeve 1011b at a location that is diametrically opposed to 1009b. The sleeve 1011a similarly includes hole 1009a formed through a wall of 1011a and a second hole (not illustrated) formed through the wall at a location that is diametrically opposed to 1009a.

It should be noted that although each of the ferrules 1005a, 1005b includes two key ways, an embodiment may also include a varying number of one or more key ways in accordance with the number of keys utilized.

What will now be described is an example illustrating how the fourth embodiment of the connector may be assembled. The following also illustrates use of pins as keys and the use of grooves, such as 1005b and its diametrically opposed groove described above, formed in the outer surface of the ferrule as key ways to prevent rotation of the ferrule. As an example of how the connector is assembled, the positioning tool may be inserted into a cavity 1052a of the corresponding sleeve 1009a and the compression fitting for that cavity tightened so that the positioning tool is positioned in the body 1006. Ferrule 1004b having a first conduit inserted therethrough may be inserted into cavity 1052b of sleeve 1009b. The ferrule 1004b is positioned in 1052b so that the groove 1005b and its diametrically opposed groove formed in the outer surface of ferrule 1004b are aligned, respectively, with hole 1009b, and its diametrically opposed hole formed through the wall of the sleeve 1011b. A pin, such as a metallic pin, may be inserted into each of holes 1009b and its corresponding diametrically opposed hole formed in sleeve 1011b. Compression fitting 1002b may then be tightened to position the first conduit in the body 1006 so that, as described above, an end of the first conduit is compressed against an end of the tip portion of the positioning tool. As the compression fitting 1002b is tightened, the ferrule 1004b is prevented from rotating due to the engagement of a first of the two pins inserted into the sleeve 1009b within the groove 1005b, and a second of the two pins in a second groove that is diametrically opposed to groove 1005b. Once the first conduit is in position, the positioning tool may be removed. Ferrule 1004a having a second conduit therethrough may be placed into cavity 1052a of sleeve 1011a in a manner similar to that as described in connection with ferrule 1004b so that groove 1004a, and its diametrically opposed groove formed in an outer surface of ferrule 1004b, are aligned, respectively, with hole 1009a and its diametrically opposed hole formed in sleeve 1009a. Pins may be inserted into each of the foregoing holes in sleeve 1009a. Compression fitting 1002a may then be tightened to position the second conduit in the body 1006.

Figure 5C:
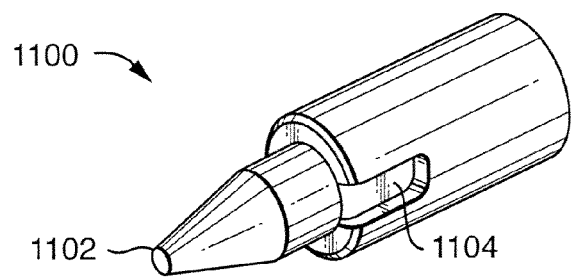
Figure 5D:
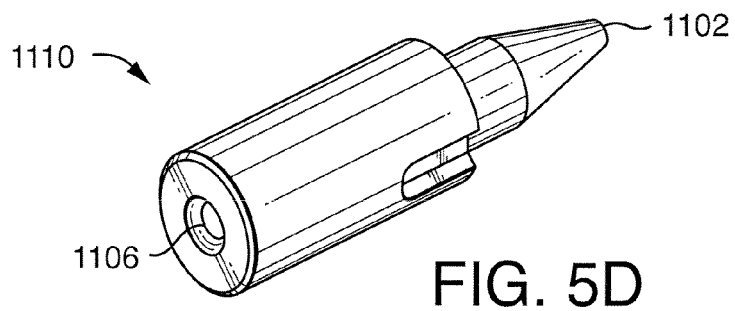
Figure 5E:
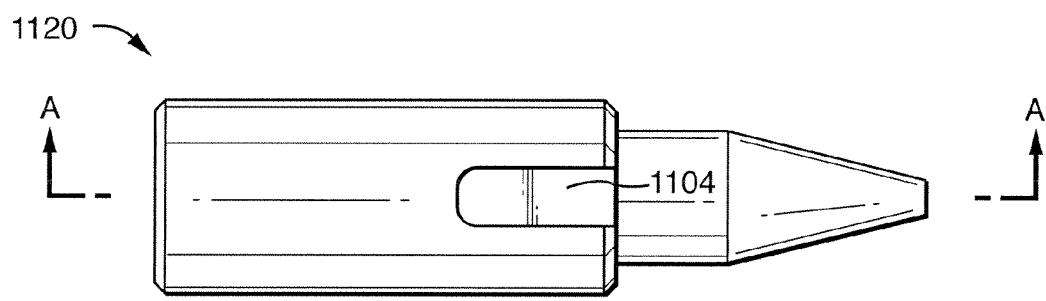
Figure 5F:
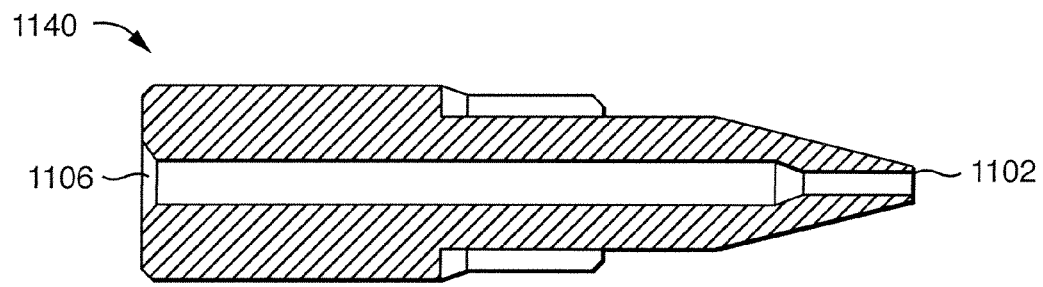

Referring to FIGS. 5C, 5D, 5E, and 5F, shown are different views of the ferrule 1004a, 1004b in accordance with an embodiment of the invention. FIG. 5C illustrates a key way 1104 and an opening 1102 at a first end of a bore through the ferrule through which the conduit extends. FIG. 5D illustrates a second opening 1106 of the bore through the ferrule. The second opening 1106 is in a second end opposing the first end. FIG. 5E is a side view of the ferrule with the keyway 1104 facing. FIG. 5F is a lateral cross-sectional view taken along A-A of FIG. 5E.

Figure 5G:
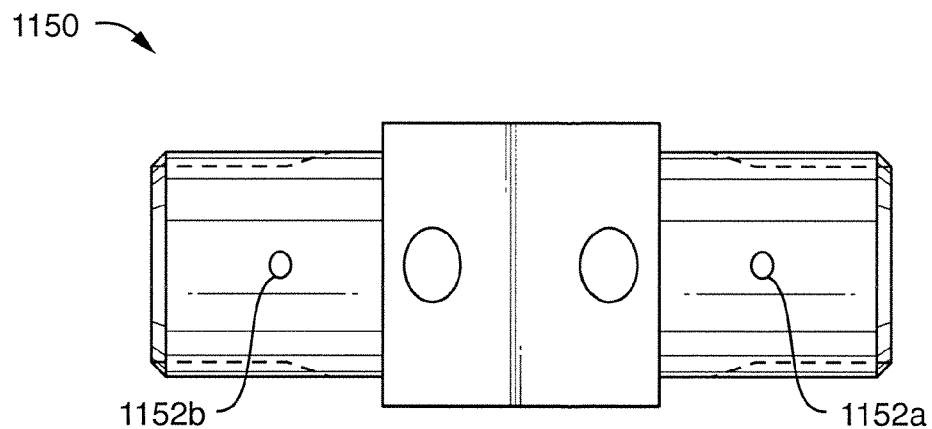
Figure 5H:
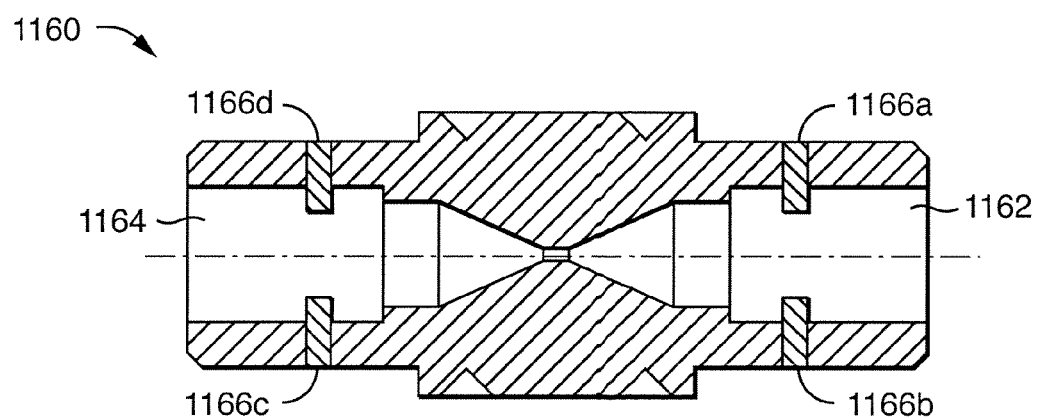

Referring to FIGS. 5G and 5H, shown are different views of the body 1006 in accordance with an embodiment of the invention. FIG. 5G shows a side view of the body and illustrates the holes 1152a and 1152b through which the pins, serving as keys, are inserted. Elements 1152a, 1152b correspond, respectively, to 1009b, 1009a of FIG. 5B. Elements 1166a-d represent portions of the outer surface of the body that are threaded to mate with threads on inner surfaces of the compression fittings, such as illustrated in FIG. 2A. Not illustrated from the views in FIGS. 5G and 5H are the two holes which are diametrically opposed to 1152a and 1152b.

In connection with the fourth embodiment, the location of the grooves in the ferrules serving as key ways and the location of the holes in the body through which pins serving as keys are inserted may vary than as described herein. It will also be appreciated by those skilled in the art that, as with all embodiments in accordance with the invention, the number of keys and mated key ways, the physical aspects of the keyways (e.g., shape, size and the like of the key ways) and keys may vary from that described herein. For example, as with other ferrules used in other embodiments, the number of keys utilized may be one or more.

As will be appreciated by those skilled in the art, the key and key way as described in connection with the fourth embodiment (in which a non-keyed ferrule is used) may be used with modified versions of the first and second embodiments described herein. For example, in the first embodiment where the ferrule holder is integrated into the body, a design similar to that as described in connection with the fourth embodiment may be used. The detachable ferrule holders may be modified to include holes therein as described in connection with the holes in sleeves 1110a, 1110b into which pins are inserted to secure the non-keyed ferrules.

With reference to the ferrules described herein, an embodiment may include a ferrule formed as a single unit as described above. Alternatively, an embodiment may utilize a two-part ferrule in which each part may comprise different materials. For example, with reference to FIG. 2B, a two part ferrule may comprise two parts partitioned as indicated by line X-X so that the tapered portion is included in a first part with the remainder of the ferrule included in the second part. The first part may be made, for example, of a PEEK material and the second part may be made of PEEK or a metal.

What will now be described are additional embodiments of connectors in accordance with the invention which utilize an elastomeric core rather than a ferrule. Additionally, there are no keys and mated key ways utilized. Rather, the elastomeric core prevents the conduit from rotating.

Figure 7A:
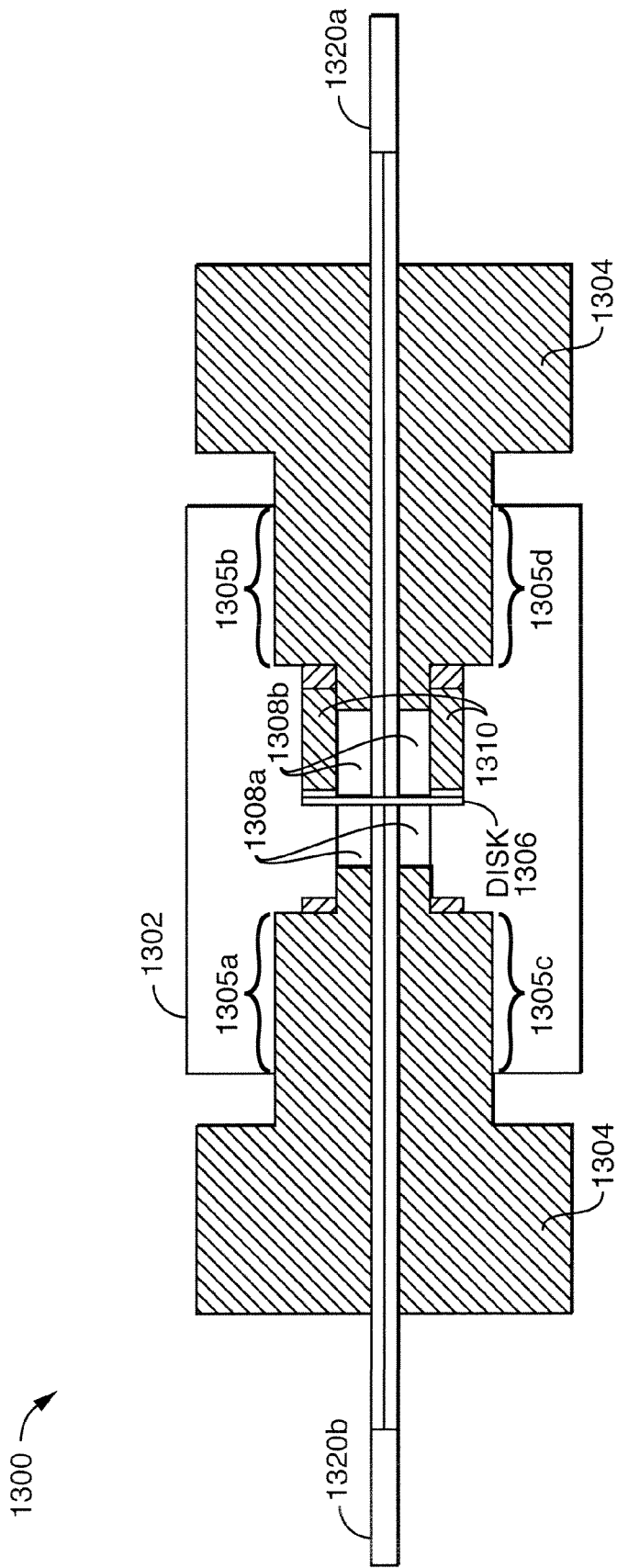

Referring to FIG. 7A, shown is an example of cutaway view of a connector including a body into which an elastomeric core is inserted into the bore of the body in accordance with an embodiment of the invention. The example 1300 includes a body 1302 of the connector, conduits 1320a, 1320b, two compression fittings 1304, an elastomeric core 1308a, 1308b, disc 1306, disc retention component 1310. The compression fittings 1304 have been threaded into the body 1302 to bear upon the ends of the core 1308. Two conduits

1320a, 1320b have been inserted through bores in compression fittings 1304 and through bores in the elastomeric core 1308. The conduits 1320a, 1320b meet within elastomeric core at a point at which the disc 1306 is located. In this example, the disc 1306 may be located at about the midpoint of the body. It should be noted that the midpoint has been selected for purposes of illustration and the point at which the two conduits come into contact within the connector may vary.

As described in connection with the first and second embodiments, the disc 1306 functions as a mechanical stop used to position the conduits 1320a, 1320b within the body 1302. Tightening of the compression fittings 1304 imparts an axial compression on elastomeric core 1308a, 1308b which, since prevented from expanding radially outwards by the bore in body 1302, compresses radially inwards and against the conduits to seal them. Furthermore, the conduits are girdled in the elastomeric core 1308a, 1308b and the axial forces exerted by tightening the compression fittings 1304 cause the conduits to move toward one another and compress against the disc 1306. Thus, the disc 1306 functions as a mechanical stop to position the conduits 1320a, 13020b as axial forces are applied with the compression fittings 1320a, 1320b are tightened.

The elastomeric core 1308a, 1308b may have an outer diameter (OD) that equals or is slightly smaller than the inner diameter (ID) of the bore through the body. The elastomeric core 1308a, 1308b may also have an OD that is larger than the ID of the bore through the body so that when the core 1308a, 1308b is compressed such as when placed in the bore of the body, the core 1308a, 1308b fits snuggly therein. Suitable materials for the elastomeric core include flexible, inert elastomeric polymers and co-polymers. Additional suitable materials and fabrication methods for the elastomeric core are described, for example, in US Patent Publication 2007/0164562, filed Nov. 28, 2006, METHOD AND APPARATUS FOR CONNECTING SMALL DIAMETER TUBING, Valaskovic, et al., which is incorporated by reference herein. The elastomeric core in this embodiment may comprise two portions 1308a, 1308b.

The disc 1306 may be made of an electrically conductive material, such as a metal, as well as other materials as described above. Furthermore, other types of mechanical stops besides a disc 1306 may be used in the embodiment of FIG. 7A as also described above. The conduits 1320a, 1320b, body 1302, and compression fittings 1304 may comprise materials and be accordingly fabricated as described elsewhere herein. The body 1302 may include threaded portions 1305a-d on inner surfaces that mate with corresponding threaded portions of outer surfaces of compression fittings 1304. In one embodiment, the body 1302 and disc 1306 may be electrically conductive materials, such as metal. As described elsewhere herein, providing an electrically conductive path to the fluid flowing in the two conduits being joined with the connector may be desirable in accordance with the particular use of the connector so that a voltage applied to the body results in applying a voltage to the fluid path.

The disc retention component 1310 may be made of suitable materials such as, for example, metals, PEEK, or other materials. A suitable fabrication method may be used in accordance with the material(s) comprising 1310.

Figure 7B:
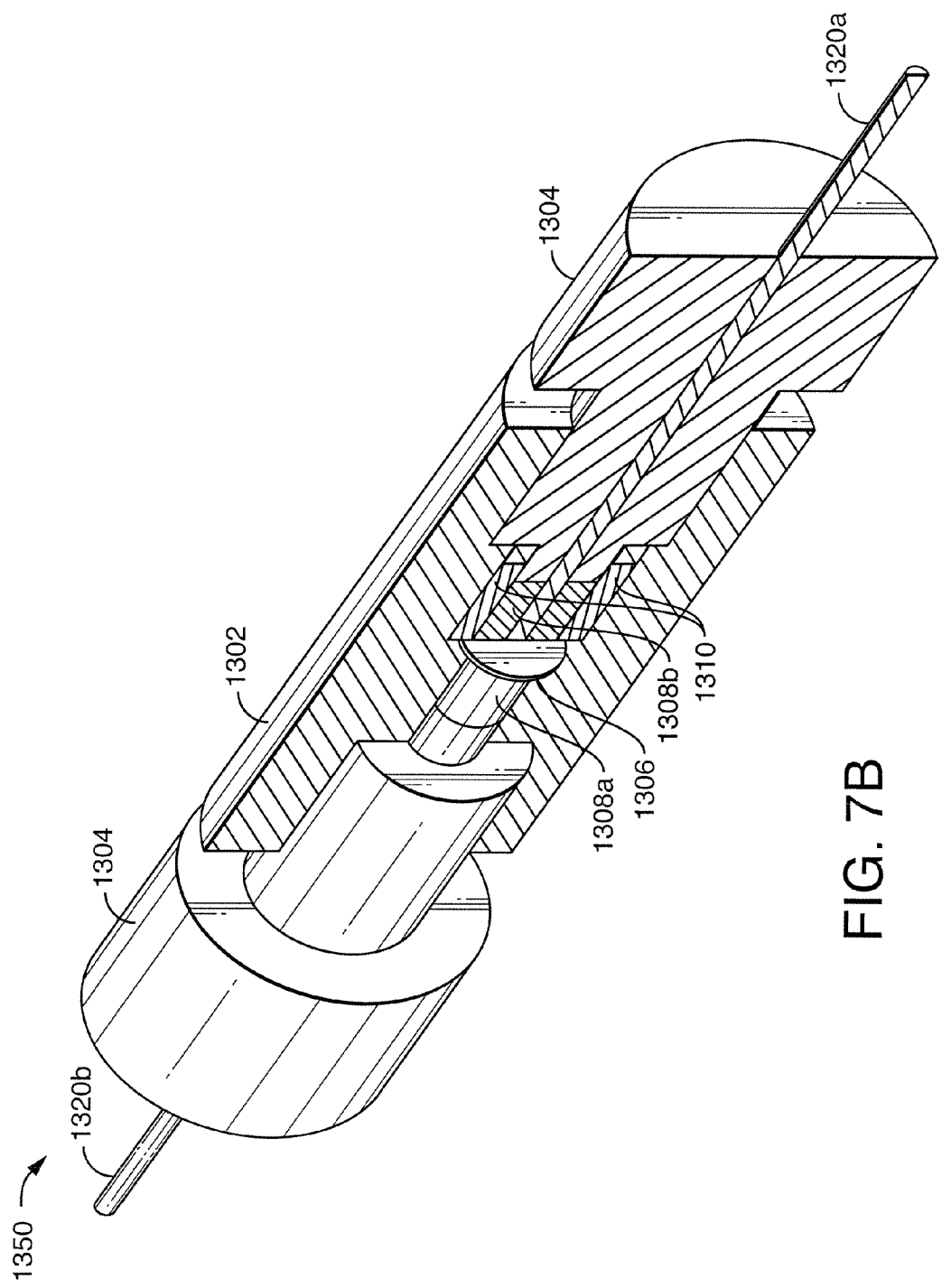

Referring to FIG. 7B, shown is a three-dimensional cutaway view of the connector of FIG. 7A.

What will now be described is one exemplary disassembled view and method of assembly of the connector illustrated in FIGS. 7A, 7B in accordance with an embodiment of the invention.

Referring to FIG. 7C, the body 1404 may be formed with an interior passageway formed therethrough as illustrated with a cavity 1402a into which the disc 1408 is inserted. Elements 1406a-d refer to the threaded inner surfaces of the body as described above. The cavity 1402a may include a first recessed portion 1403 configured to have dimensions selected in accordance with the dimensions of the disc 1408. The first recessed portion 1403 may include a wall 1405 which is formed approximately perpendicular to the center radial axis of the body and which has a length L slightly larger than the OD of the disc 1408. A hole 1407 is also formed in the wall 1405 connecting cavity 1402a to another cavity 1402b.

Figure 7D:
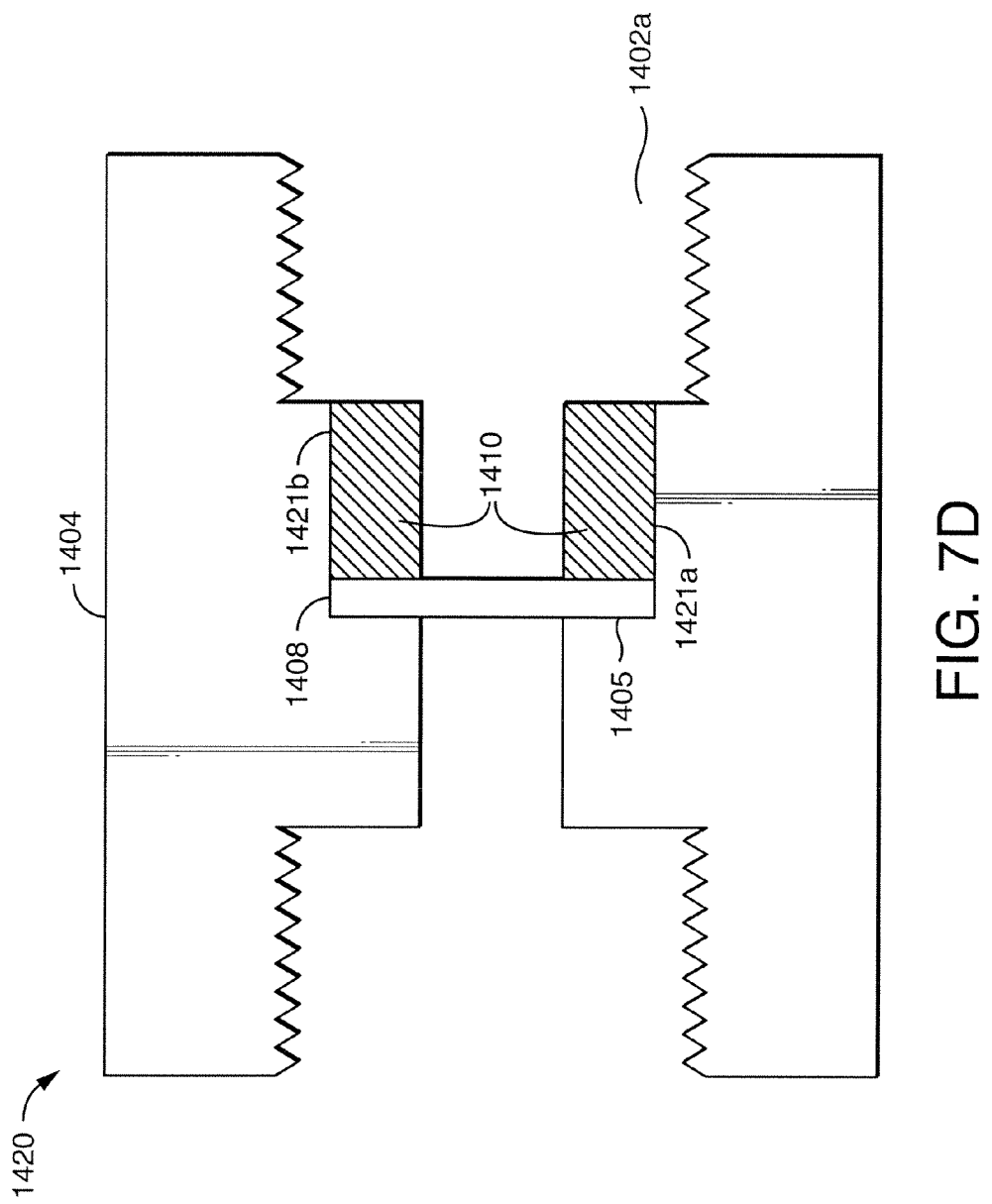

Referring to FIG. 7D, the disc 1408 is positioned in the cavity 1402 as illustrated and flush against wall 1405. The disc retention component 1410 may be inserted to retain the disc in position. The component 1410 may be secured to the inner walls of the body 1404 using any suitable means known in the art. As an example, the component 1410 may be secured using an adhesive. The length of walls 1421a, 1421b of the first recessed portion which are approximately parallel to the center radial axis of the body have a length selected in accordance with dimensions of the component 1410 so that component 1410 approximately extends the length of the walls 1421a, 1421b when inserted into position to secure the disc 1408.

Figure 7E:
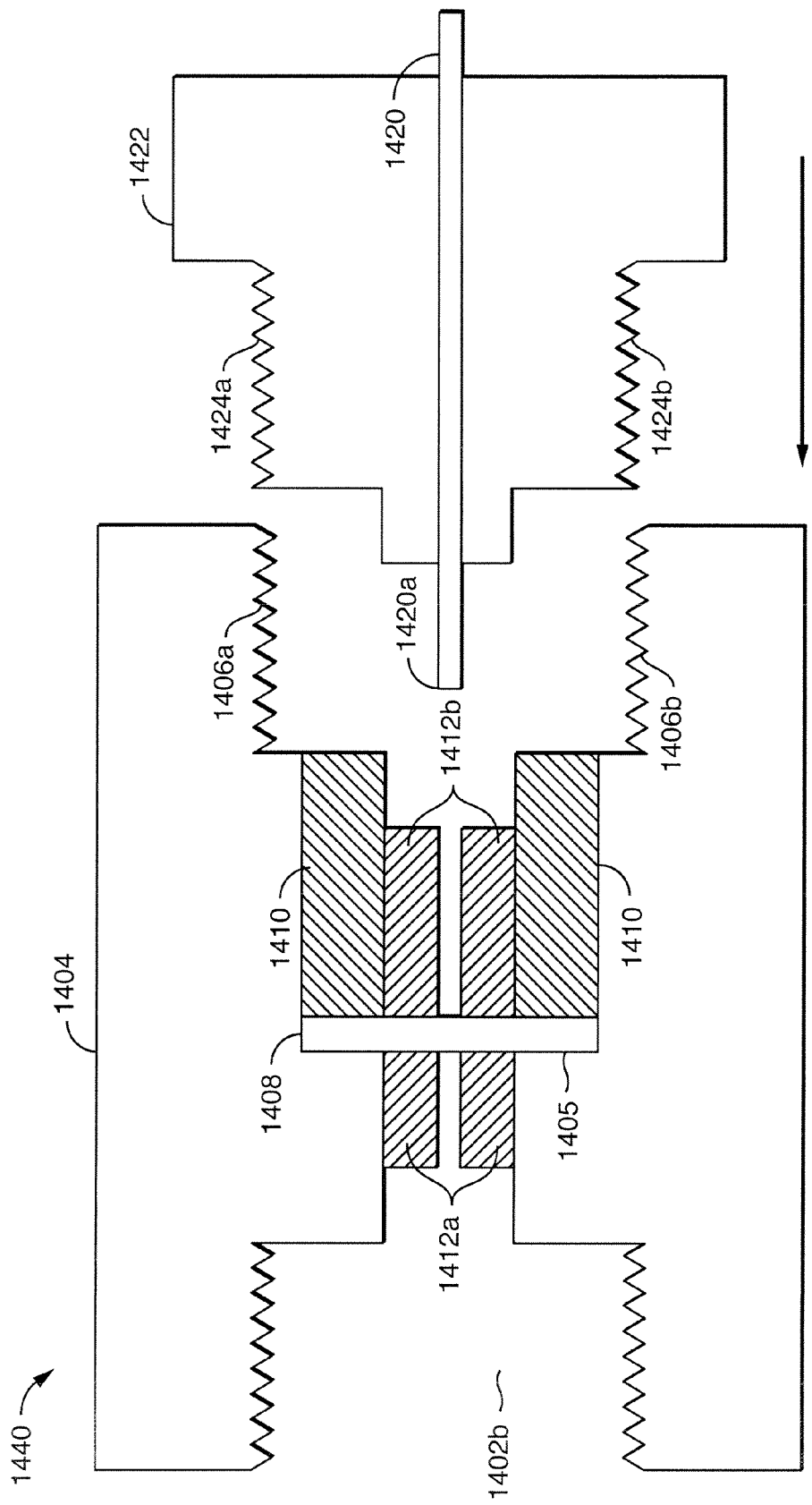

Referring to FIG. 7E, the elastomeric core portions 1412a, 1412b are inserted and may be secured using any suitable means such as, for example, an adhesive. The assembled disc retention component 1410 and elastomeric core portion 1412b may have shape and dimensions configured in accordance with the compression fitting 1422 and conduit 1420 inserted in a bore through the fitting 1422. The compression fitting 1422 includes threaded portions 1424a, 1424 on an outer surface that mate with threaded portions 1406a, 1406b on an inner surface of the body.

The conduit 1420 is inserted into the bore through the fitting 1422 and a bore through the elastomeric core portion 1412b. As the compression fitting 1422 is tightened, the elastomeric core portion 1412b is axially compressed in combination with substantially preventing radial expansion of the elastomeric core portion 1412b resulting in imparting an inward radial compression to the elastomeric core portion 1412b to sealingly engage the conduit 1420 inserted into the elastomeric core portion 1412b. The forces applied during compression of fitting 1422 also cause the conduit 1420 to axially compress against the disc 1408 so that an end 1420a of the conduit is compressed against the disc 1408 when inserted into position within the core portion 1412b. Thus, a fluidic seal is created by the outward radial expansion of the elastomeric core portion 1412b against the disc retention component 1410, the inward radial compression of the elastomeric core portion 1412b around the conduit 1420 and the axial compression of the conduit 1420 and elastomeric core portion 1412b against the disc. The conduit 1420 inserted into the bore of the elastomeric core portion 1412b may have an outer diameter which approximates but is less than the diameter of the bore through 1412b.

Although only a single compression fitting and conduit inserted therethrough is illustrated, a second compression fitting including a second conduit inserted therethrough may be positioned into cavity 1402b by tightening the second compression fitting in a manner similar to that as described for the fitting 1422.

In connection with the embodiment described in FIGS. 7A-7E, an elastomeric core including two portions is used to create a fluidic seal against both the disc and the conduits. The seal is created when the compression fittings, such as threaded screws, are tightened as described above. Additionally, with reference to FIG. 7E, the forces applied during tightening of the compression fitting 1422 cause the core portion 1412*b* to expand radially outward against the disc retention component, to expand radially inward against the conduit, and to be axially compressed (along with the conduit inserted therethrough) against the disc creating a fluidic seal. In connection with the second compression fitting and second conduit inserted into cavity 1402*b*, tightening of the second compression fitting (not illustrated) causes the core portion 1412*a* to expand radially outward against walls of the cavity 1402*b*, to expand radially inward against the second conduit, and to be axially compressed (along with the second conduit inserted therethrough) against the disc creating a fluidic seal.

Figure 7F:
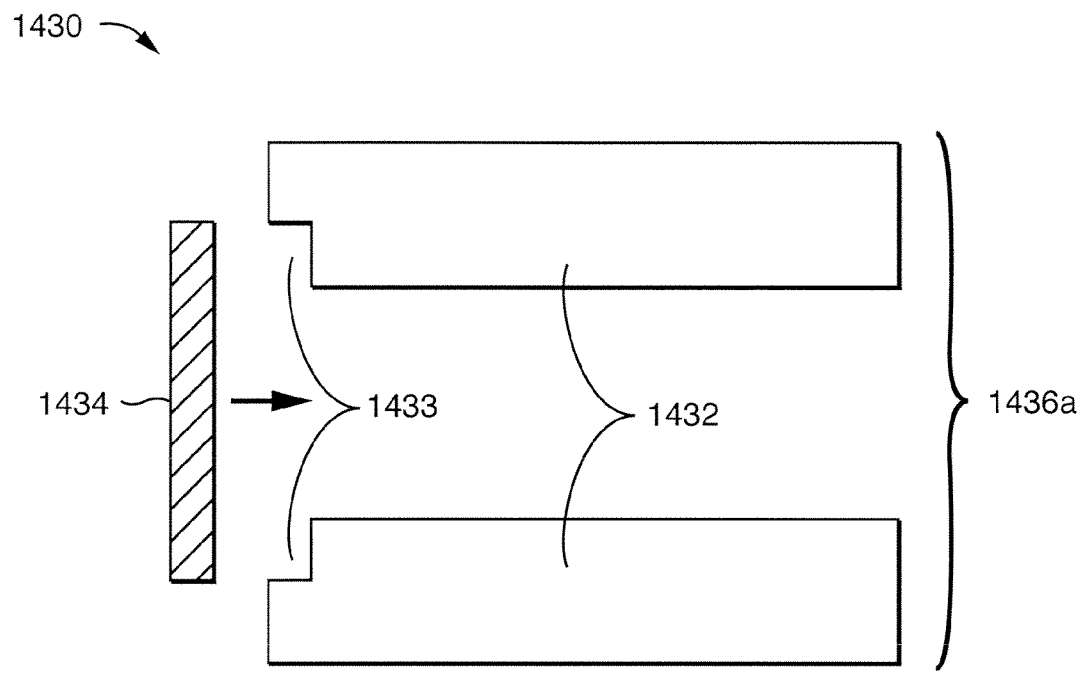
Figure 7G:
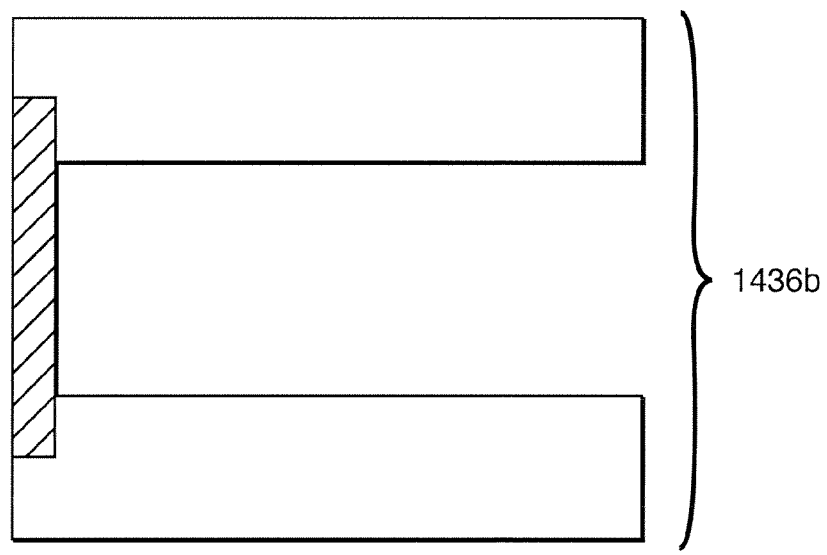

With reference to FIG. 7F and 7G, shown is an alternative configuration of the disc and disc retention component as may be included in an embodiment of the connector in accordance with the invention. The example 1430 illustrates another way in which the disc 1434 and disc retention component 1432 may be configured, for example for use with the connector as illustrated in FIG. 7A and 7B. Element 1436*a* illustrates that the disc retention component 1432 is configured to receive the disc 1434. The outer diameter of 1434 is less than the outer diameter of 1432 and 1432 is configured to have a recessed portion 1433 on a surface that mates with the disc 1434. Element 1436*a* shows the disc 1434 and the disc retention component 1432 prior to assembly. As a step in assembling the connector, the disc 1434 may be positioned in the disc retention component 1432 as illustrated in 1436*a* of FIG. 7F resulting in the illustration of 1436*b* of FIG. 7G. The combined disc 1434 and disc retention component 1432 of 1436*b* may then be placed in position in the body.

It should be noted that the elastomeric core may be used in other embodiments of the connector as described herein in place of the ferrule. Additionally, such embodiments may omit keys and mated key ways used to prevent rotation of the conduit since such rotation is substantially prevented by the elastomeric core. As an example, an embodiment of the connector in accordance with the invention may use components described in connection with FIG. 1A and may omit features thereof used to form keys and key ways preventing rotation of the conduits. In particular, the embodiment may use the body 20, compression fittings 10*a*, 10*b*, and detachable ferrule holder 14. In place of the ferrules 12*a* and 12*b*, elastomeric core portions may be used. A first conduit may be inserted in a bore through a first elastomeric core portion used in place of ferrule 12*b*. A second conduit may be inserted in a bore through a second elastomeric core portion used in place of ferrule 12*a*. As another example, an embodiment of the connector in accordance with the invention may use components described in connection with FIG. 3A and may omit features thereof used to form keys and key ways preventing rotation of the conduits. In particular, the embodiment may use the body 550, compression fittings 510*a*, 510*b*, and detachable ferrule holders 530*a*, 530*b*. In place of the ferrules 520*a* and 520*b*, elastomeric core portions may be used. A first conduit may be inserted in a bore through a first elastomeric core portion used in place of ferrule 520*a*. A second conduit may be inserted in a bore through a second elastomeric core portion used in place of ferrule 520*b*. In the foregoing embodiments using the elastomeric core portions, the detachable ferrule holders may alternatively be referred to more generally as detachable holders which hold the elastomeric core portions. Also, cavities in the foregoing bodies and detachable holders holding the elastomeric core portions may be configured to have shape and dimensions in accordance with the core portions rather than as configured for the ferrules.

What will now be described is a variation of the embodiment illustrated in FIGS. 7A and 7B using a two-part body.

Figure 8A:
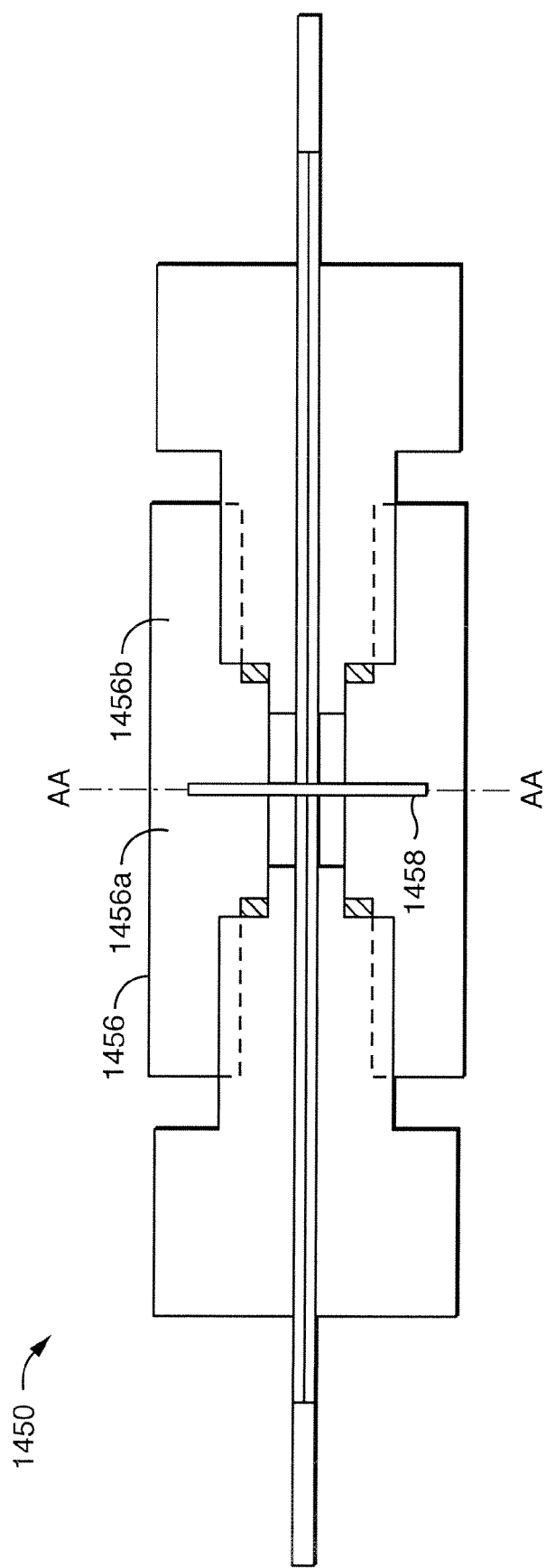
Figure 8B:
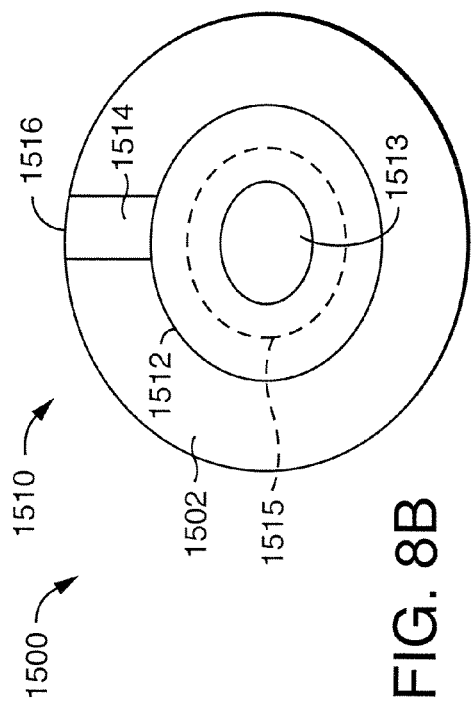
Figure 8C:
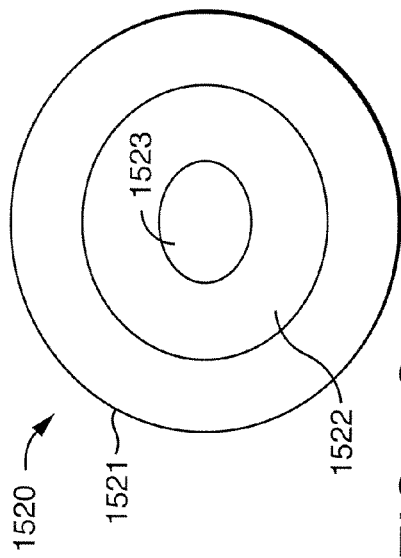
Figure 8D:
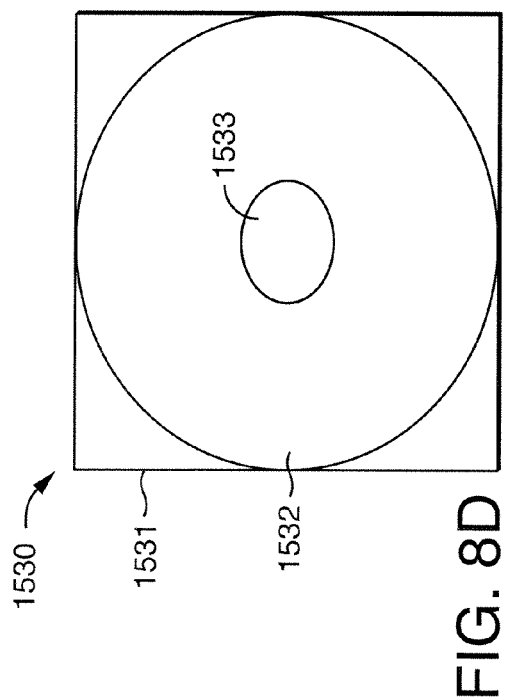
Figure 8E:
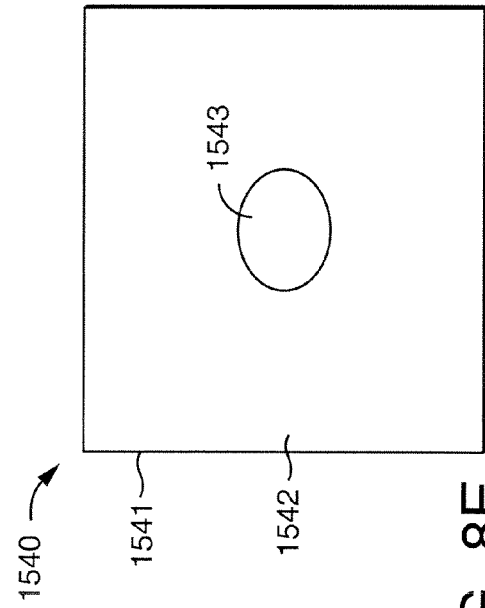

Referring to FIG. 8A, shown is an example of cutaway view of a connector including a two-part body into which an elastomeric core is inserted into the bore of the body in accordance with an embodiment of the invention. The components of FIG. 8A are similar to those as described in connection with FIG. 7A with the variation that the disc retention component is omitted, and the body 1456 comprises two parts 1456*a*, 1456*b* partitioned along line AA-AA. The disc retention component is omitted because the disc is retained by and positioned within the two-part body as will be described. Each of the body parts 1456*a*, 1456*b* may be fabricated separately and then secured together along AA-AA using any one of variety of different suitable methods. For example, one of 1456*a*, 1456*b* may include a threaded inner surface that mates with a threaded outer surface of the other of 1456*a*, 1456*b*. The two parts of the body may be secured in a manner similar to that as described herein when positioning the ferrule holder in a body of the connector. The two parts may also be secured using other suitable means such as suitable adhesive or bonding techniques. Prior to securing together 1456*a* and 1456*b*, the disc 1458 may be inserted therebetween. The outer diameter of the disc may be the same or less than the outer diameter of the body 1456 and the two inwardly facing surfaces of the two parts 1456*a*, 1456*b* facing toward one another along line AA-AA may be configured to receive the disc 1458 so that when assembled, the disc 1458 is secured in position between 1456*a* and 1456*b*.

Referring to FIGS. 8B-8E, shown are examples of cutaway views taken along line AA-AA when the disc is secured in position as illustrated in FIG. 8A. The example 1500 illustrates 4 views in FIGS. 8B-8E with the disc positioned on top of one of the foregoing two inwardly facing surfaces. Elements 1510 of FIG. 8B and 1520 of FIG. 8C correspond to an embodiment in which the circumference of the body is rounded and may approximate a circular shape. In 1510, the disc is represented by elements 1512 and 1514 in combination. The disc may be formed as a single unit or a two-part component (e.g., a first part corresponding to 1512 and a second part corresponding to 1514.) Element 1512 has a hole 1513 therethrough forming a fluidic port through which fluid passes between the conduits positioned in a body. Also illustrated is an exemplary conduit outer circumference 1515 for relative comparison purposes. Element 1502 represents the outer surface of the body. The design of 1510 may be used, for example, in an embodiment in which the body may be electrically nonconductive and the disc formed from 1512 and 1514 is electrically conductive. Portion 1514 may be exposed at an area of the surface 1516 of the body so that a voltage can be applied to the portion of 1514 exposed at the surface to provide an electrically conductive path to the fluid passing through 1513. Depending on the position of the connector in a system, it may be desirable to provide such an electrically path to the fluid as illustrated in more detail in following paragraphs and figures.

The second view 1520 illustrates the outer surface 1521 of the body and disc 1522 including a hole 1523 therethrough serving as a fluidic port. Elements 1520 illustrates use of a disc as described herein in connection with other embodiments.

In the third and fourth views, square-shaped bodies are illustrated. In 1530, element 1531 may represent the outer surface of the body. Element 1532 represents the disc having hole 1533 formed therethrough serving as a fluidic port. In 1540, element 1541 may represent the outer surface of the body and also the outer surface of the disc 1542. In other words, the disc 1542 may be configured to have an outer surface in accordance with the outer surface 1541 of the body. Element 1543 may represent a hole formed through the disc 1542 in which 1543 serves as a fluidic port.

Use of a two-part body as described above provides a continuous seal between the body and the disc when assembled. The two-part body may also allow for higher attainable fluidic pressure in a system utilizing an embodiment of the connector such as, for example, in an LC system.

Referring to FIGS. 8F and 8G, shown are examples illustrating the exertion of forces upon components of a connector using in an embodiment in accordance with the invention which result in a fluidic seal. The illustrations 140 and 147 are cutaway views. For purposes of illustration, the disc 144 in this example may be incorporated as an integral part of the body although the disc or other stop may be positioned in the body using other suitable techniques. It should be noted that the illustration and description of FIGS. 8F and 8G are applicable to embodiments utilizing the ferrule as described herein as well as those embodiments in which the elastomeric core is used as an alternative to the ferrule. Examples 140 and 147 refer to a sealing member which is a general term used to describe a function of both the elastomeric core and ferrule in embodiments described herein. Thus, the sealing member 146 in FIGS. 8F, 8G may be either the ferrule or the elastomeric core depending on the particular connector embodiment.

In FIG. 8F, components of the connector and conduits are illustrated prior to tightening the compression fitting. The example 140 includes a bore 142 extending through the connector body, disc 144, sealing member 146, bore 141 extending through the ferrule 146, and conduit 143. The conduit 143 has inner walls 143a and outer walls 143b. The conduit 143 is inserted through bore 141 of the sealing member 146. The sealing member 146 is inserted into the bore 142 of the body. Element 145 represents the area at which compressive force is applied as the compression fitting (not shown) is tightened. As described above, the diameter D1 of the hole in disc 144 is selected to be less than D2, the OD of the conduit 143. Lengths M1 and M2 represent the area of contact between the conduit and the disc when the conduit 143 is in position after tightening of the compression fitting.

In FIG. 8G, the compression fitting has been tightened and causes the sealing member to expand radially outward against the inner walls of the bore 142 of the body. As the compression fitting is further tightened, the inner walls of the bore in the body substantially prevent further outward radial expansion so that the sealing member 146 in the body expands radially inward against the conduit to sealingly engage the conduit. Also, the sealing member 146 and conduit 143 are compressed against the disc 144. The sealing member 146 is used to form a fluidic seal between the inner walls of the body and the conduit, and between the disc and the conduit.

It should be noted that an embodiment may use ferrules which are not tapered (as illustrated in the examples 140, 147) or are alternatively tapered in a different manner than as described herein with the cavities receiving the ferrules accordingly configured. FIGS. 8F and 8G are also exemplary illustrations in which the ferrule is inserted directly into the body so that the ferrule holder is incorporated as an integral part of the body, for example, as described above in connection with ferrule 12b of FIGS. 1A, 1B. With a detachable ferrule holder, forces are exerted in a manner similar to as just described with the difference being that the ferrule is inserted in a cavity of the detachable ferrule holder so that the seal formed involves the inner walls of the cavity in the detachable ferrule holder rather than the inner walls of the body.

In connection with the embodiments described herein, a fluidic seal as provided by a sealing member, such as a ferrule or elastomeric core or other deformable fitting, may provide a substantially fluid-tight seal.

Figure 9:
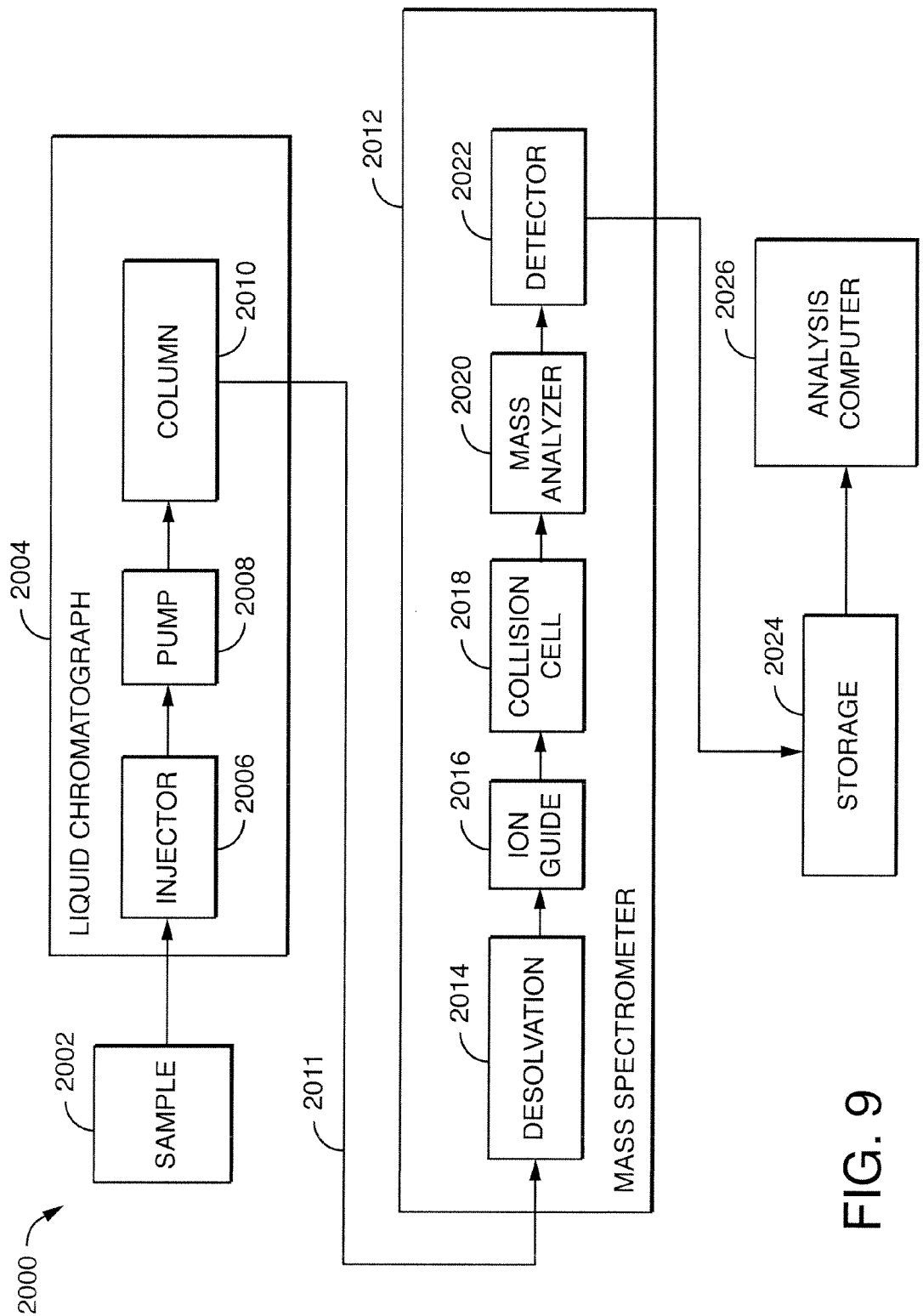
FIG. 9 is an example illustrating use and placement of a connector in accordance with the invention in a system.

Referring to FIG. 9, shown is a block diagram of an LC/MS system 2000 in which an embodiment of the connector in accordance with the invention may be utilized. The system 2000 includes a chromatography (LC) module 2004 and a mass-spectrometer (MS) module 2012 that receives an eluent from the chromatography module 2004. The LC module 2004 includes an injector 2006 that receives a sample 2002, a pump 2008 and a column 2010. The MS module 2012 includes a desolvation/ionization device 2014, an ion guide 2016, a mass analyzer 2020, and a detector 2022. The system 2000 also includes a data storage unit 2024 and a computer module 2026. The computer module 2026 may be connected to modules 2004 and/or 2012, for example, to automate processing, control components, and the like.

In operation, the sample 2002 is injected into the LC module 2004 via the injector 2006. The pump 2008 pumps the sample through the column 2010 to separate the mixture into component parts according to retention time through the column 2010.

The output from the column 2010 is input to a mass spectrometer 2012 for analysis. Initially, the sample is desolvated and ionized by the desolvation/ionization device 2014. Any desolvation technique can be employed, including, for example, a heater, a gas, and a heater in combination with a gas or other desolvation technique. Ionization can be by any suitable ionization technique, including for example, electrospray ionization (ESI), atmospheric pressure chemical ionization (APCI), or other ionization technique. Ions resulting from the ionization are fed to a collision cell 2018 by the ion guide 2016. The collision cell 2018 is used to fragment the ions. The output of the collision cell 2018 is input to a mass analyzer 2020. The detector 2022 detects ions emanating from the mass analyzer 2020. The detector 2022 is optionally integrated with mass analyzer 2020.

Any one of the embodiments of the connector described herein may be used at various points two connect two conduits. For example, a connector may be positioned for use in connecting two conduits within a module, such as within 2004, or interfacing two modules, such as 2004 and 2012. As a further example, a connector may be positioned at some point between 2004 and 2012, such as at the point identified by 2011, to interface a first capillary tubing out of column 2010 with a second capillary tubing extending to the inlet of the MS module 2012. In an MS module 2012, for example, which performs ESI, the connector may have an electrically conductive disc and an electrically conductive body. A voltage may be applied, for example, to the body of the connector and the combination of the body and disc provides a conductive path to the fluid in the tubing so that the fluid becomes electrically conductive for use in connection with the ESI process. The foregoing is just one placement and use of the connectors described herein as may be utilized in an embodiment. The connector herein may be more generally be used to connect any two components.

As will be appreciated by those skilled in the art, use of the key and key ways as described herein are illustrated with embodiments of connectors for connecting two conduits. Additionally, as will be appreciated by those skilled in the art, the foregoing keys and key ways may also be incorporated into other connectors which connecting more than two conduits. Similarly, the use of a stop to position conduits in the body may also be incorporated into other connectors which connect more than two conduits.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A connector for connecting a first conduit to a second conduit comprising:
 a body having a passageway through the body, a first cavity being at a first end of the passageway and a second cavity at a second end of the passageway, wherein the first and second cavities are aligned along a common central axis of the body;
 a first sealing member providing a substantially fluid tight seal for the first conduit, said first cavity receiving a first detachable holder whereby the first detachable holder receives said first sealing member, said first sealing member having the first conduit inserted therethrough;
 a second sealing member providing a substantially fluid tight seal for the second conduit, said second cavity directly receiving said second sealing member, said second sealing member having the second conduit inserted therethrough;
 a first compression fitting for compressing the first sealing member by applying forces to the first sealing member, the forces including a rotational force;
 a first set of one or more keys and one or more mated key ways which are engageable to prevent rotation of the first conduit when the first sealing member is compressed, wherein the one or more keys of the first set are part of the first sealing member and the one or more mated key ways of the first set are included in the first detachable holder;
 a second compression fitting for compressing the second sealing member by applying forces to the second sealing member, the forces including a rotational force; and
 a second set of one or more keys and one or more mated key ways which are engageable to prevent rotation of the second conduit when the second sealing member is compressed, wherein the one or more keys of the second set are part of the second sealing member and the one or more mated key ways of the second set are included in the body, and wherein the first sealing member is a ferrule that includes at least one key of said first set, and wherein said second sealing member is a ferrule that includes at least one key of said second set.

2. The connector of claim 1, further comprising a stop located in the body for indicating an insertion point for the first and the second conduits, wherein the stop and the body are electrically conductive and included in an electrically conductive path to fluid that passes between the first and the second conduits.

3. A connector for connecting a first conduit to a second conduit comprising:
 a body having a passageway therethrough, a first cavity being at a first end of the passageway and a second cavity at a second end of the passageway, wherein the first and second cavities are aligned along a common central axis of the body;
 a first sealing member for providing a substantially fluid tight seal for the first conduit;
 a second sealing member for providing a substantially fluid tight seal for the second conduit;
 a first compression fitting for compressing the first sealing member by applying forces to the first sealing member, the forces including a rotational force;
 a second compression fitting for compressing the second sealing member by applying forces to the second sealing member, the forces including a rotational force;
 a first set of one or more keys and one or more mated key ways for preventing rotation of the first conduit when the first sealing member is compressed; and
 a second set of one or more keys and one or more mated key ways for preventing rotation of the second conduit when the second sealing member is compressed, wherein the first cavity receives a first detachable holder whereby the first detachable holder receives the first sealing member and the second cavity in the body receives the second sealing member, wherein the one or more keys of the first set are part of the first sealing member and the one or more mated key ways of the first set are included in the first detachable holder, and wherein the one or more keys of the second set are part of the second sealing member and the one or more mated key ways of the second set are included in the body, and wherein the first sealing member comprises a ferrule that includes the one or more keys of the first set and wherein the second sealing member comprises a ferrule that includes the one or more keys of the second set.

4. The connector of claim 3,
wherein the first detachable holder is engageable with the first compression fitting and the first detachable holder is engageable with the body, and wherein the second compression fitting is enageable with the body, and wherein the first detachable holder includes a first threaded portion of an outer surface threaded to mate with a second threaded portion on an inner surface of the first compression fitting, the first detachable holder including a third threaded portion of an outer surface threaded to mate with a fourth threaded portion on an inner surface of the body, and wherein the second compression fitting includes a fifth threaded portion on an inner surface to mate with a sixth threaded portion on an outer surface of body.

5. The connector of claim 3,
wherein the first detachable holder is engageable with the first compression fitting and the first detachable holder is engageable with the body, and wherein the second compression fitting is enageable with the body, and wherein each of the one or more mated key ways in the first set is a groove formed in the first detachable holder.

6. The connector of claim 3,
wherein the first detachable holder is engageable with the first compression fitting and the first detachable holder is engageable with the body, and wherein the second compression fitting is enageable with the body, and wherein each of the one or more mated key ways in the second set is a groove formed in the body.

7. The connector of claim 3, further comprising:
 a stop indicating an insertion point in the body for the first conduit and the second conduit.

8. The connector of claim 3, wherein each of the compression fittings is engageable with the housing or a detachable holder for compressing one of the sealing members, and the connector further comprises a stop indicating an insertion point in the body for the first conduit and the second conduit, wherein the stop is electrically conductive, and wherein the body is electrically conductive.

9. The connector of claim 3, wherein each of the compression fittings is engageable with the housing or a detachable holder for compressing one of the sealing members, and the connector further comprises a stop indicating an insertion point in the body for the first conduit and the second conduit, wherein the stop is electrically conductive, and wherein the stop is included in an electrically conductive path to fluid passing through the first and the second conduits in the body.

10. The connector of claim 3, wherein the first sealing member has a through bore and wherein, upon insertion of the first conduit into the through bore, placement of the first sealing member in one of the first cavity in the body, the second cavity in the body or another cavity in the detachable holder, and tightening of the first compression fitting to thereby exert a compressive force, axial compression of the first sealing member in combination with substantially preventing outward radial expansion of the first sealing member by the one cavity imparts an inward radial compression to the first sealing member to sealingly engage the first conduit.

11. The connector of claim 3, wherein the second sealing member has a through bore and wherein, upon insertion of the second conduit into the through bore, placement of the second sealing member in one of the first cavity in the body, the second cavity in the body or another cavity in the detachable holder, and tightening of the second compression fitting to thereby exert a compressive force, axial compression of the second sealing member in combination with substantially preventing outward radial expansion of the second sealing member by the one cavity imparts an inward radial compression to the second sealing member to sealingly engage the second conduit.

12. The connector of claim 3, wherein the first set includes two keys and two mated key ways and wherein the second set includes two keys and two mated key ways.

13. The connector of claim 3, wherein each of the compression fittings is engageable with the housing or a detachable holder for compressing one of the sealing members, and the connector further comprises a stop indicating an insertion point in the body for the first conduit and the second conduit, and wherein the first sealing member has a through bore and wherein, upon insertion of the first conduit into the through bore, placement of the first sealing member in one of the first cavity in the body, the second cavity in body or another cavity in the detachable holder, and tightening of the first compression fitting to thereby exert a compressive force, axial compression of the first sealing member towards the stop in combination with substantially preventing outward radial expansion of the first sealing member by walls of the one cavity imparts an inward radial compression to the first sealing member to sealingly engage the first conduit providing a substantially fluid tight seal between the first conduit, the walls of the one cavity, and the stop.

14. The connector of claim 3, wherein each of the compression fittings is engageable with the housing or a detachable holder for compressing one of the sealing members, and the connector further comprises a stop indicating an insertion point in the body for the first conduit and the second conduit, and wherein the second sealing member has a through bore and wherein, upon insertion of the second conduit into the through bore, placement of the second sealing member in one of the first cavity in the body, the second cavity in body or another cavity in the detachable holder, and tightening of the second compression fitting to thereby exert a compressive force, axial compression of the second sealing member towards the stop in combination with substantially preventing outward radial expansion of the second sealing member by walls of the one cavity imparts an inward radial compression to the second sealing member to sealingly engage the second conduit providing a substantially fluid tight seal between the second conduit, the walls of the one cavity, and the stop.

\* \* \* \* \*